(12) United States Patent  
Guillemont et al.

(10) Patent No.: US 7,902,225 B2  
(45) Date of Patent: Mar. 8, 2011

(54) MYCOBACTERIAL INHIBITORS

(75) Inventors: Jérôme Emile Georges Guillemont, Ande (FR); Elisabeth Therese Jeanne Pasquier, Le Neubourg (FR); David Francis Alain Lancois, Louviers (FR)

(73) Assignee: Janssen Pharmaceutica NV, Beerse (BE)

( * ) Notice: Subject to any disclaimer, the term of this patent is extended or adjusted under 35 U.S.C. 154(b) by 665 days.

(21) Appl. No.: 10/596,270

(22) PCT Filed: Jan. 21, 2005

(86) PCT No.: PCT/EP2005/050271  
§ 371 (c)(1),  
(2), (4) Date: Jun. 7, 2006

(87) PCT Pub. No.: WO2005/070430  
PCT Pub. Date: Aug. 4, 2005

(65) Prior Publication Data  
US 2007/0093478 A1    Apr. 26, 2007

(51) Int. Cl.  
C07D 215/38    (2006.01)  
A61K 31/04    (2006.01)

(52) U.S. Cl. .......... 514/312; 514/611; 546/159; 546/167

(58) Field of Classification Search .................. 514/311, 514/312; 546/159, 167  
See application file for complete search history.

(56) References Cited

U.S. PATENT DOCUMENTS

| 5,965,572 | A | 10/1999 | Ellis et al. | |
|---|---|---|---|---|
| 7,652,014 | B2 * | 1/2010 | Mabire et al. | 514/253.07 |
| 2007/0072842 | A1 * | 3/2007 | Dominique et al. | 514/217.06 |
| 2007/0129375 | A1 * | 6/2007 | Mabire et al. | 514/249 |
| 2008/0249099 | A1 * | 10/2008 | Mabire et al. | 514/249 |
| 2008/0255116 | A1 * | 10/2008 | Andries et al. | 514/235.2 |
| 2009/0042881 | A1 * | 2/2009 | Mabire et al. | 514/235.2 |

FOREIGN PATENT DOCUMENTS

| WO | 00/34265 A2 | 6/2000 |
|---|---|---|
| WO | 00/43383 A1 | 7/2000 |
| WO | 00/78748 A1 | 12/2000 |
| WO | 01/07432 A2 | 2/2001 |
| WO | WO 02/056882 A1 | 7/2002 |
| WO | WO 2004/002490 A2 | 1/2004 |
| WO | WO 2004/011436 A1 | 2/2004 |

OTHER PUBLICATIONS

Wommack, J of Med Chem, vol. 14(12), pp. 1218-1219, 1971.*  
Wommack, J.B. et al., Journal of Medicinal Chemistry, vol. 12, No. 14, pp. 1218-1220, 1971.

* cited by examiner

Primary Examiner — D. Margaret Seaman  
(74) Attorney, Agent, or Firm — Thomas Dodd

(57) ABSTRACT

The present invention relates to novel substituted quinoline derivatives according to the general Formula (Ia) or the general Formula (Ib)

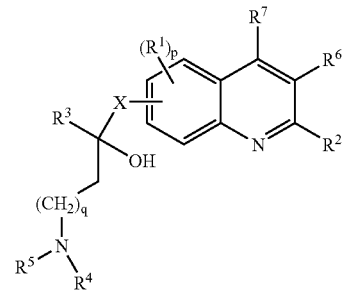

(Ia)

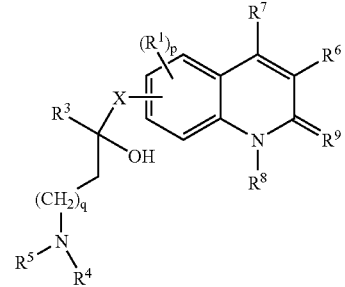

(Ib)

the pharmaceutically acceptable acid or base addition salts thereof, the quaternary amines thereof, the stereochemically isomeric forms thereof the tautomeric forms thereof and the N-oxide forms thereof. The claimed compounds are useful for the treatment of mycobacterial diseases. In particular, compounds are claimed in which, independently from each other, $R^1$ is halo; p=1; $R^2$ is optionally substituted alkyloxy, alkyl, Ar, Het, or a radical of formula

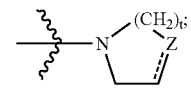

$R^3$ is optionally substituted Ar or Het; q=1, $R^4$ and $R^5$ each independently are alkyl; $R^6$ is hydrogen or a radical of formula

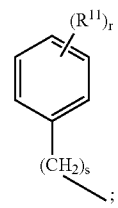

r is equal to 0 or 1 and $R^7$ is hydrogen or Ar. Also claimed is a composition comprising a pharmaceutically acceptable carrier and, as active ingredient, a therapeutically effective amount of the claimed compounds, the use of the claimed compounds or compositions for the manufacture of a medicament for the treatment of mycobacterial diseases and a process for preparing the claimed compounds.

14 Claims, No Drawings

MYCOBACTERIAL INHIBITORS

The present invention relates to novel substituted quinoline derivatives useful for the treatment of mycobacterial diseases, particularly those diseases caused by pathogenic mycobacterial such as *Mycobacterium tuberculosis (M.), M. bovis, M. avium* and *M. marinum*.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide.

Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a flier seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together, the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed Obviously, a compound that reduces both the total length of treatment and the frequency of drug administration would provide the greatest benefit Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and can not be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against MDR strains.

The term "drug resistant" as used hereinbefore or hereinafter is a term well understood by the person skilled in microbiology. A drug resistant *Mycobacterium* is a *Mycobacterium* which is no longer susceptible to at least one previously effective drug, which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

MDR tuberculosis is a specific form of drug resistant tuberculosis due to a bacterium resistant to at least isoniazid and rifampicin (with or without resistance to other drugs), which are at present the two most powerful anti-TB drugs.

The purpose of the present invention is to provide novel compounds, in particular substituted quinoline derivatives, having the property of inhibiting growth of Mycobacterial including drug resistant or multi drug resistant Mycobacterial, and therefore useful for the treatment of mycobacterial diseases, particularly those diseases caused by pathogenic mycobacterial such as *Mycobacterium tuberculosis, M. bovis, M. avium, M. smegmatis* and *M. marinum*.

Substituted quinolines were already disclosed in U.S. Pat. No. 5,965,572 (The United States of America) for treating antibiotic resistant infections and in WO 00/34265 to inhibit the growth of bacterial microorganisms. WO 2004/011436 describes quinoline derivatives as antimycobacterial agents.

SUMMARY OF THE INVENTION

The present invention relates to novel substituted quinoline derivatives according to Formula (Ia) and (I-b).

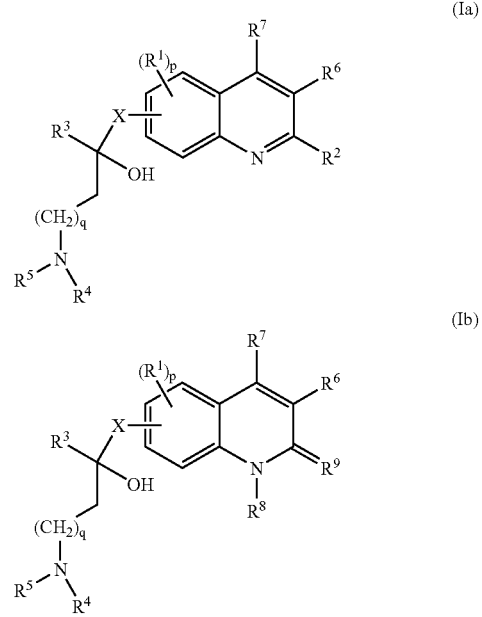

the pharmaceutically acceptable acid or base addition salts thereof, the quaternary amines thereof, the stereochemically isomeric forms thereof, the tautomers forms thereof and the N-oxide forms thereof, wherein:

$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2 or 3;

$R^2$ is hydrogen; alkyl; hydroxy; thio; alkyloxy optionally substituted with amino or mono or di(alkyl)amino or a radical of formula

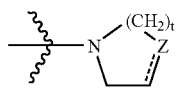

wherein Z is $CH_2$, $CH-R^{10}$, O, S, $N-R^{10}$ and t is an integer equal to 1 or 2 and the dotted line represents an optional bond; alkyloxyalkyloxy; alkylthio; mono or di(alkyl)amino wherein alkyl may optionally be substituted with one or two substituents each independently be selected from alkyloxy or Ar or Het or morpholinyl or 2-oxopyrrolidinyl; Ar, Het or a radical of formula

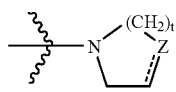

wherein Z is $CH_2$, $CH-R^{10}$, O, S, $N-R^{10}$; t is an integer equal to 1 or 2; and the dotted line represents an optional bond;

$R^3$ is alkyl Ar, Ar-alkyl, Het or Het-alkyl;

q is an integer equal to zero, 1, 2, 3 or 4;

X is a direct bond or $CH_2$;

$R^4$ and $R^5$ each independently are hydrogen, alkyl or benzyl; or $R^4$ and $R^5$ together and including the N to which they are attached may form a radical selected from the group of pyrrolidinyl, 2H-pyrrolyl, 2-pyrrolinyl, 3-pyrrolinyl, pyrrolinyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, each of said rings optionally being substituted with alkyl, halo, haloalkyl, hydroxy, alkyloxy, amino, mono- or dialkylamino, alkylthio, alkyloxyalkyl, alkylthioalkyl and pyrimidinyl;

$R^6$ is hydrogen or a radical of formula

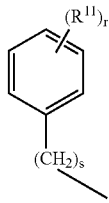

wherein s is an integer equal to zero, 1, 2, 3 or 4; r is an integer equal to 1, 2, 3, 4 or 5; and $R^{11}$ is hydrogen, halo, haloalkyl, hydroxy, Ar, alkyl, alkyloxy, alkylthio, alkyloxyalkyl, alkylthioalkyl, Ar-alkyl or di(Ar)alkyl ; or two vicinal $R^{11}$ radicals may be taken together to form together with the phenyl ring to which they are attached a naphthyl;

$R^7$ is hydrogen, alkyl Ar or Het;

$R^8$ is hydrogen or alkyl;

$R^9$ is oxo; or $R^8$ and $R^9$ together form the radical $-C=CH-N=$;

$R^{10}$ is hydrogen, alkyl, hydroxyl, aminocarbonyl, mono or di(alkyl)aminocarbonyl, Ar, Het, alkyl substituted with one or two Het, alkyl substituted with one or two Ar, Het-C(=O)—, Ar—C(=O)—;

alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms ; wherein each carbon atom can be optionally substituted with halo, hydroxy, alkyloxy or oxo;

Ar is a homocycle selected from the group of phenyl, naphthyl, acenaphthyl, tetrhydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, alkylcarbonyl, aminocarbonyl, morpholinyl and mono- or dialkylaminocarbonyl;

Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl pyrazinyl and pyridazinyl; or a bicyclic heterocycle selected from the group of quinolinyl, isoquinolinyl, 1,2,3,4tetrahydroisoquinolinyl, quinoxalinyl, indolyl, indazolyl, benzimidazolyl, benzoxazolyl, benzisoxazolyl, benzothiazole, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms.

provided that when $R^7$ is hydrogen then the

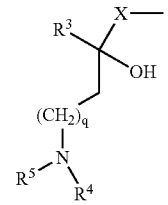

radical may also be placed in position 3 of the quinoline ring.

The compounds according to Formula (Ia) and (Ib) are interrelated in that e.g. a compound according to Formula (Ib), with $R^9$ equal to oxo is the tautomers equivalent of a compound according to Formula (Ia) with $R^2$ equal to hydroxy (keto-enol tautomerism).

DETAILED DESCRIPTION

In the framework of this application, alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo.

Preferably, alkyl is methyl, ethyl or cyclohexylmethyl.

$C_{1-6}$alkyl as a group or part of a group encompasses the straight and branched chain saturated hydrocarbon radicals having from 1 to 6 carbon atoms such as, methyl, ethyl, butyl, pentyl, hexyl, 2-methylbutyl and the like.

In the framework of this application, Ar is a homocycle selected from the group of phenyl naphthyl, acenaphthyl, tetrhydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl. Preferably, Ar is naphthyl or phenyl, each optionally substituted with 1 or 2 substituents selected from halo or alkyl, preferably halo.

In the framework of this application, Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrazinyl and pyridazinyl; or a bicyclic heterocycle selected from the group of quinolinyl, isoquinolinyl 1,2,3,4-tetrahydroisoquinolinyl, quinoxalinyl, indolyl, indazolyl, benzimidazolyl, benzoxazolyl, benzoxazolyl, benzothiazole, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy. Preferably, Het is thienyl, furanyl imidazolyl, pyridyl, triazolyl, benzo[1,3]dioxolyl, indazolyl, isoquinolinyl, 1,2,3,4tetrahydroisoquinolinyl, benzofuranyl.

In the framework of this application, halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms. Preferably, halo is bromo, fluoro or chloro and preferably, haloalkyl is trifluoromethyl.

In the framework of this application, the quinoline ring of the compounds of formula (Ia) or (Ib) is numbered as follows:

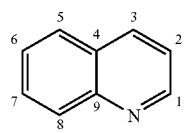

The

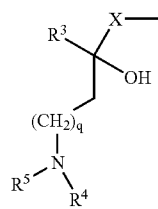

radical may be placed on any available position of the quinoline moiety.

Whenever used hereinafter, the term "compounds of formula (Ia) or (Ib)" is meant to also include their N-oxide forms, their salts, their quaternary amines, their tautomers forms and their stereochemically isomeric forms. Of special interest are those compounds of formula (Ia) or (Ib) which are stereochemically pure.

An interesting embodiment of the present invention relates to those compounds of formula (Ia) or (Ib), the pharmaceutically acceptable acid or base addition salts thereof, the stereochemically isomeric forms thereof, the tautomers forms thereof and the N-oxide forms thereof, wherein $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2 or 3;

$R^2$ is hydrogen; alkyl; hydroxy; thio; alkyloxy optionally substituted with amino or mono or di(alkyl)amino or a radical of formula

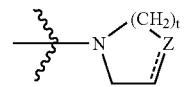

wherein Z is $CH_2$, $CH-R^{10}$, O, S, $N-R^{10}$ and t is an integer equal to 1 or 2 and the dotted line represents an optional bond; alkyloxyalkyloxy; alkylthio; mono or di(alkyl)amino wherein alkyl may optionally be substituted with one or two substituents each independently be selected from alkyloxy or Ar or Het or morpholinyl or 2-oxopyrrolidinyl; Het or a radical of formula

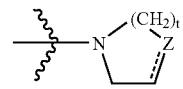

wherein Z is $CH_2$, $CH-R^{10}$, O, S, $N-R^{10}$; t is an integer equal to 1 or 2; and the dotted line represents an optional bond;

$R^3$ is alkyl, Ar, Ar-alkyl Het or Het-alkyl;

q is an integer equal to zero, 1, 2, 3 or 4;

X is a direct bond;

$R^4$ and $R^5$ each independently are hydrogen, alkyl or benzyl; or $R^4$ and $R^5$ together and including the N to which they are attached may form a radical selected from the group of pyrrolidinyl 2H-pyrrolyl, 2-pyrrolinyl, 3-pyrrolinyl, pyrrolyl, imidazolidinyl, pyrazolidinyl, 2-imidazolinyl 2-pyrazolinyl, imidazolyl pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, each of said rings optionally being substituted with alkyl, halo, haloalkyl, hydroxy, alkyloxy, amino, mono- or diallcylamino, alkylthio, alkyloxyallyl, alkylthioalayl and pyrimidinyl;

$R^6$ is a radical of formula

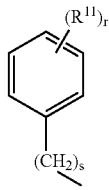

wherein s is an integer equal to zero, 1, 2, 3 or 4; r is an integer equal to 1, 2, 3, 4 or 5; and $R^{11}$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^{11}$ radicals may be taken together to form together with the phenyl ring to which they are attached a naphthyl;
$R^7$ is hydrogen, alkyl, Ar or Het;
$R^8$ is hydrogen or alkyl;
$R^9$ is oxo; or
$R^8$ and $R^9$ together form the radical —CH=CH—N=;
$R^{10}$ is hydrogen, alkyl, aminocarbonyl, mono-or di(alkyl)aminocarbonyl, Ar, Het, alkyl substituted with one or two Het, alkyl substituted with one or two Ar, Het-C(=O)—;
alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;
Ar is a homocycle selected from the group of phenyl, naphthyl acenaphthyl, tetrhydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl alkyloxycarbonyl, alkylcarbonyl, aminocarbonyl, morpholinyl and mono- or dialkylaminocarbonyl;
Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrzinyl and pyridazinyl; or a bicyclic heterocycle selected from the group of quinolinyl, quinoxalinyl, indolyl, indazolyl, benidazolyl, benzoxazolyl, benzoxazolyl, benzothiazole, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;
halo is a substituent selected from the group of fluoro, chloro, bromo and iodo and
haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms.

Preferably, $R^{11}$ is hydrogen, halo, haloalkyl, hydroxy, Ar, alkyl, alkyloxy, alkylthio, alkyloxyalkyl, alkylthioalkyl, Ar-alkyl or di(Ar)alkyl.

Preferably, when $R^6$ is other than hydrogen then $R^7$ is hydrogen and when $R^7$ is other than hydrogen then $R^6$ is hydrogen.

Preferably, $R^6$ is other than hydrogen and $R^7$ is hydrogen.

Preferably, $R^7$ is other than hydrogen and $R^6$ is hydrogen.
Preferably, the invention relates to compounds of Formula (Ia) and (Ib) wherein:
$R^1$ is hydrogen, halo, cyano, Ar, Het, alkyl, and alkyloxy;
p is an integer equal to 1, 2 or 3;
$R^2$ is hydrogen; alkyl; hydroxy; alkyloxy optionally substituted with amino or mono or di(alkyl)amino or a radical of formula

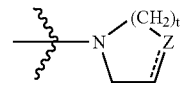

wherein Z is $CH_2$, CH—$R^{10}$, O, S, N—$R^{10}$ and t is an integer equal to 1 or 2 and the dotted line represents an optional bond; alkyloxyalkyloxy; alkylthio; mono or di(alkyl)amino; Ar; Het or a radical of formula

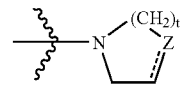

wherein Z is $CH_2$, CH—$R^{10}$, O, S, N—$R^{10}$; t is an integer equal to 1 or 2; and the dotted line represents an optional bond;
$R^3$ is alkyl, Ar, Ar-alkyl or Het;
q is an integer equal to zero, 1, 2, or 3
X is a direct bond or $CH_2$;
$R^4$ and $R^5$ each independently are hydrogen, alkyl or benzyl; or
$R^4$ and $R^5$ together and including the N to which they are attached may form a radical selected from the group of pyrrolidinyl, imidazolyl, triazolyl, piperidinyl, piperazinyl, pyrazinyl, morpholinyl and thiomorpholinyl, optionally substituted with alkyl and pyrimidinyl;
$R^6$ is hydrogen or a radical of formula

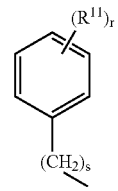

wherein s is an integer equal zero, 1, 2, 3 or 4; r is an integer equal to 1, 2, 3, 4 or 5; and $R^{11}$ is hydrogen, halo, or alkyl; or two vicinal $R^{11}$ radicals may be taken together to form together with the phenyl ring to which they are attached a naphthyl; preferably $R^{11}$ is hydrogen, halo, or alkyl;
r is an integer equal to 1;
$R^7$ is hydrogen or Ar,
$R^8$ is hydrogen or alkyl;
$R^9$ is oxo; or
$R^8$ and $R^9$ together form the radical —C=CH—N=;
alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo or hydroxy;

Ar is a homocycle selected from the group of phenyl, naphthyl, acenaphthyl, tetrhydronaphthyl, each optionally substituted with 1, 2 or 3 substituents, each substituent independently selected from the group of halo, haloalkyl, cyano, alkyloxy and morpholinyl;

Het is a monocyclic heterocycle selected from the group of N-phenoxypiperidinyl, pyrrolyl, pyrazolyl imidazolyl, furanyl, thienyl, oxazolyl, isoxazolyl, thiazolyl, isothiazolyl triazolyl, pyridinyl, pyrimidinyl, pyrazinyl and pyridazinyl; or a bicyclic heterocycle selected from the group of quinolinyl, isoquinolinyl, 1,2,3,4tetrahydroisoquinolinyl, quinoxalinyl, indolyl, indazolyl, benzimidazolyl, benzoxazolyl, benzoxazolyl, benzothiazole, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy; and halo is a substituent selected from the group of fluoro, chloro and bromo.

For compounds according to either Formula (Ia) and (Ib), preferably, $R^1$ is hydrogen, halo, Ar, Het, alkyl or alkyloxy. More preferably, $R^1$ is hydrogen, halo, alkyl or Het. Even more in particular $R^1$ is hydrogen, halo or Het. Most preferably, $R^1$ is halo, in particular bromo.

Preferably, p is equal to 1.

Preferably, $R^2$ is hydrogen; alkyl; alkyloxy optionally substituted with amino or mono or di(alkyl)amino or a radical of formula

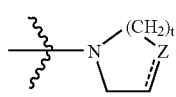

wherein Z is $CH_2$, $CH-R^{10}$, O, S, $N-R^{10}$ and t is an integer equal to 1 or 2 and the dotted line represents an optional bond; mono or di(alkyl)amino; Ar, Het or a radical of formula

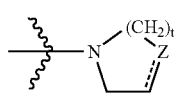

wherein Z is $CH_2$, $CH-R^{10}$, O, S, $N-R^{10}$; t is an integer equal to 1 or 2; and the dotted line represents an optional bond. More preferably, $R^2$ is alkyloxy, Het, Ar, alkyl, mono or di(alkyl)amino, a radical of formula

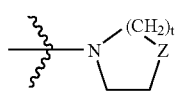

wherein Z is $CH_2$, $CH-R^{10}$, O, $N-R^{10}$; t is an integer equal to 1 or 2; alkyloxy substituted with amino or mono or di(alkyl)amino or a radical of formula

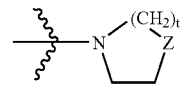

wherein Z is $CH_2$, $CH-R^{10}$, O, $N-R^{10}$ and t is an integer equal to 1 or 2. Most preferably, $R^2$ is alkyloxy, e.g. methyloxy; Het or a radical of formula

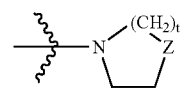

wherein Z is $CH_2$, $CH-R^{10}$, O, $N-R^{10}$ and t is 1 or 2.

Preferably, $R^3$ is naphthyl, phenyl or Het, each optionally substituted with 1 or 2 substituents, that substituent preferably being a halo or haloalkyl, most preferably being a halo. More preferably, $R^3$ is naphthyl, phenyl, 3,5-dihalophenyl, 1,6-dihalophenyl, thienyl, furanyl, benzofuranyl, pyridyl. Most preferably, $R^3$ is optionally substituted phenyl, e.g. 3,5-dihalophenyl, or naphthyl.

Preferably, q is equal to zero, 1 or 2. More preferably, q is equal to 1.

Preferably, $R^4$ and $R^5$ each independently are hydrogen or alkyl, more preferably hydrogen, methyl or ethyl, most preferably methyl.

Preferably $R^4$ and $R^5$ together and including the N to which they are attached form a radical selected from the group of imidazolyl, triazolyl, piperidinyl, piperazinyl and thiomorpholinyl, optionally substituted with alkyl, halo, haloalkyl, hydroxy, alkyloxy, alkylthio, alkyloxyalkyl or alkylthioalkyl, preferably substituted with alkyl, most preferably substituted with methyl or ethyl.

Preferably, $R^6$ is hydrogen or a radical of formula

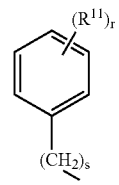

wherein s is an integer equal to zero, 1 or 2, preferably zero or 1; r is an integer equal to 1 or 2, preferably 1; and $R^{11}$ is hydrogen, halo, or alkyl, preferably hydrogen or alkyl. More preferably, $R^6$ is a radical of formula

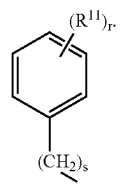

Most preferably, $R^6$ is benzyl or phenyl. Preferably r is 1 and $R^{11}$ is hydrogen.

Preferably, $R^7$ is hydrogen, alkyl or Ar. More preferably hydrogen or Ar, in particular hydrogen or phenyl. Most preferably $R^7$ is hydrogen.

For compounds according to Formula (Ib) only, preferably, $R^8$ is alkyl or hydrogen, preferably hydrogen, and $R^9$ is oxygen.

Preferably, $R^{10}$ is hydrogen, alkyl, hydroxyl, alkyl substituted with one or two Het, alkyl substituted with one or two Ar, Het-C(=O)—. Most preferably $R^{10}$ is hydroxyl, Het, alkyl substituted with one Het, alkyl substituted with one Ar.

Preferably the compounds of the present invention are compounds according to Formula (Ia), the pharmaceutically acceptable acid or base addition salts thereof, the quaternary amines thereof, the stereochemically isomeric forms thereof the tautomers forms thereof and the N-oxide forms thereof Preferably X is a direct bond.

Preferably X is $CH_2$.

An interesting group of compounds are those compounds according to Formula (Ia) or (Ib), preferably (Ia), the pharmaceutically acceptable acid or base addition salts thereof, the quaternary amines thereof the stereochemically isomeric forms thereof, the tautomers forms thereof and the N-oxide forms thereof, in which $R^1$ is hydrogen, halo, Ar, alkyl or alkyloxy; p=1; $R^2$ is hydrogen, alkyloxy or alkylthio, $R^3$ is naphthyl, phenyl or thienyl, each optionally substituted with 1 or 2 substituents selected from the group of halo and haloalkyl; q=0, 1, 2 or 3; $R^4$ and $R^5$ each independently are hydrogen or alkyl or $R^4$ and $R^5$ together and including the N to which they are attached form a radical selected from the group of imidazolyl, triazolyl, piperidinyl, piperazinyl and thiomorpholinyl; $R^6$ is hydrogen, alkyl or halo; r is equal to 1 and $R^7$ is hydrogen.

Also an interesting group of compounds are those compounds according to Formula (Ia) or (Ib), preferably (Ia), the pharmaceutically acceptable acid or base addition salts thereof, the quaternary amines thereof, the stereochemically isomeric forms thereof, the tautomers forms thereof and the N-oxide forms thereof wherein $R^1$ is hydrogen, halo, alkyl or Het, wherein Het is preferably pyridyl; $R^2$ is alkyl, alkyloxy optionally substituted with mono or di(alkyl)amino or a radical of formula

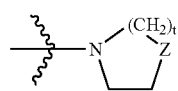

wherein Z is $CH_2$, CH—$R^{10}$, O, N—$R^{10}$, preferably Z is $CH_2$, t is an integer equal to 1 or 2, and $R^{10}$ is hydrogen, alkyl, hydroxyl alkyl substituted with one or two Het, alkyl substituted with one or two Ar, Het-C(=O)—, preferably $R^{10}$ is hydrogen; Ar, Het; a radical of formula

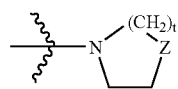

wherein Z is $CH_2$, CH—$R^{10}$, O, N—$R^{10}$, t is an integer equal to 1 or 2, wherein $R^{10}$ is hydrogen, alkyl, hydroxyl, alkyl substituted with one or two Het, alkyl substituted with one or two Ar, Het-C(=O)—; $R^3$ is Ar, preferably phenyl or naphthyl, or Het, preferably thienyl, furanyl, pyridyl, benzofuranyl, each of said Ar or Het optionally substituted with 1 or 2 substituents that substituent preferably being a halo; $R^4$ and $R^5$ are each alkyl, preferably methyl; $R^6$ is hydrogen, phenyl, benzyl or 4-methylbenzyl; $R^7$ is hydrogen or phenyl; $R^8$ is hydrogen; $R^9$ is oxo.

Interesting intermediates of the present invention are intermediates of formula

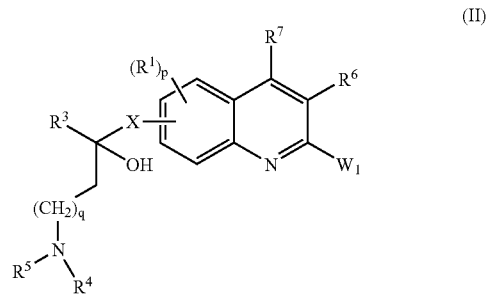

wherein $W_1$ represents a suitable leaving group, such as for example halo, e.g. chloro, bromo and the like, and wherein $R^1$, $R^3$ to $R^7$, X, q and p are as defined hereinabove.

The pharmaceutically acceptable acid addition salts are defined to comprise the therapeutically active non-toxic acid addition salt forms which the compounds according to either Formula (Ia) or (Ib) are able to form Said acid addition salts can be obtained by treating the base form of the compounds according to either Formula (Ia) or (Ib) with appropriate acids, for example inorganic acids, for example hydrophilic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to either Formula (Ia) or (Ib) containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to either Formula (Ia) or (Ib) as well as the salts thereof, are able to form. Such solvates are, for example, hydrates and alcoholates.

The term "quaternary amine" as used hereinbefore defines the quaternary ammonium salts which the compounds of formula (Ia) or (Ib) are able to form by reaction between a basic nitrogen of a compound of formula (Ia) or (Ib) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The term "stereochemically isomeric forms" as used herein defines all possible isomeric forms which the compounds of either Formula (Ia) or (Ib) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R— or S-configuration; substituents on bivalent cyclic (partially) saturated radicals may have either the cis- or trans-configuration. Stereochemically isomeric forms of the compounds of either Formula (Ia) or (Ib) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

Compounds of either Formula (Ia) and (Ib) and some of the intermediate compounds invariably have at least one stereogenic centers in their structure which may lead to at least 2 stereochemically different structures.

The compounds of either Formula (Ia) or (Ib) as prepared in the processes described below may be synthesized in the form of racemic mixtures of enantiomers which can be separated from one another following art-known resolution procedures. The racemic compounds of either Formula (Ia) or (Ib) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of either Formula (Ia) or (Ib) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomers forms of the compounds of either Formula (Ia) or (Ib) are meant to comprise those compounds of either Formula (Ia) or (Ib) wherein e.g. an enol group is converted into a keto group (keto-enol tautomerism).

The N-oxide forms of the compounds according to either Formula (Ia) or (Ib) are meant to comprise those compounds of either Formula (Ia) or (Ib) wherein one or several nitrogen atoms are oxidized to the so-called N-oxide, particularly those N-oxides wherein the nitrogen of the amine radical is oxidized.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112-176, and *Drugs*, 1985, 29, pp. 455-473.

Pro-drugs forms of the pharmacologically-active compounds according to the invention will generally be compounds according to either Formula (Ia) or (Ib), the pharmaceutically acceptable acid or base addition salts thereof, the stereochemically isomeric forms thereof, the tautomers forms thereof and the N-oxide forms thereof, having an acid group which is esterified or amidated. Included in such esterified acid groups are groups of the formula —COOR$^x$, where R$^x$ is a $C_{1-6}$alkyl, phenyl, benzyl or one of the following groups:

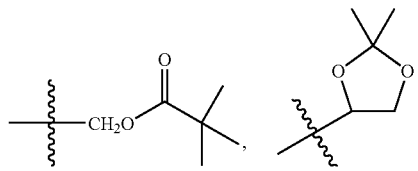

Amidated groups include groups of the formula —CONR$^y$R$^z$, wherein R$^y$ is H, $C_{1-6}$alkyl, phenyl or benzyl and R$^z$ is —OH, H, $C_{1-6}$alklyl, phenyl or benzyl.

Compounds according to the invention having an amino group may be derivatised with a ketone or an aldehyde such as formaldehyde to form a Mannich base. This base will hydrolyze with first order kinetics in aqueous solution.

The compounds according to the invention have surprisingly been shown to be suitable for the treatment of mycobacterial diseases, particularly those diseases caused by pathogenic mycobacterial, including drug resistant and multi drug resistant mycobacterial, such as *Mycobacterium tuberculosis, M. bovis, M. avium, M. smegmatis* and *M. marinum*. The present invention thus also relates to compounds of either Formula (Ia) or (Ib) as defined hereinabove, the pharmaceutically acceptable acid or base addition salts thereof, the stereochemically isomeric forms thereof, the tautomers forms thereof and the N-oxide forms thereof, for use as a medicine.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admix with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredient of formula (Ia) or (Ib), and, from 1 to 99.95% by weight, more preferably from 30 to 99.9 weight % of a pharmaceutically acceptable carrier, all percentages being based on the total composition.

The pharmaceutical composition may additionally contain various other ingredients known in the art, for example, a lubricant, stabilizing agent, buffering agent, emulsifying agent, viscosity-regulating agent, surfactant, preservative, flavoring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight Further, the present invention also relates to the use of a compound of either Formula (Ia) or (Ib), the pharmaceutically acceptable acid or base addition salts thereof, the stereochemically isomeric forms thereof, the tautomers forms thereof and the N-oxide forms thereof, as well as any of the aforementioned pharmaceutical compositions thereof for the manufacture of a medicament for the prevention or the treatment of mycobacterial diseases.

Accordingly, in another aspect, the invention provides a method of treating a patient suffering from, or at risk of, a mycobacterial disease, which comprises administering to the patient a therapeutically effective amount of a compound or pharmaceutical composition according to the invention.

The compounds of the present invention may also be combined with one or more other antimycobacterial agents.

Therefore, the present invention also relates to a combination of (a) a compound of formula (Ia) or (Ib) and (b) one or more other antimycobacterial agents.

The present invention also relates to a combination of (a) a compound of formula (Ia) or (Ib) and (b) one or more other antimycobacterial agents for use as a medicine.

A pharmaceutical composition comprising a pharmaceutically acceptable carrier and, as active ingredient, a therapeutically effective amount of (a) a compound of formula (Ia) or (Ib) and (b) one or more other antimycobacterial agents is also comprised by the present invention.

The other Mycobacterial agents which may be combined with the compounds of formula (Ia) or (Ib) are for example rifampicin (=rifampin); isoniazid; pyrazinamide; amikacin; ethionamide; moxifloxacin; ethambutol; streptomycin; para-aminosalicylic acid; cycloserine; capreomycin; kanamycin; thioacetazone; PA-824; quinolones/fluoroquinolones such as for example ofloxacin, ciprofloxacin, sparfloxacin; macrolides such as for example clarithromycin, clofazimine, amoxyciluin with clavulanic acid; rifamycins; rifabutin; rifapentine.

Preferably, the present compounds of formula (Ia) or (Ib) are combined with rifapentin and moxifloxacin.

General Preparation

The compounds according to the invention can generally be prepared by a succession of steps, each of which is known to the skilled person.

Compounds of formula (Ia) wherein $R^2$ represents alkoxy; a radical of formula

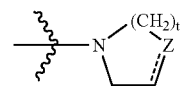

wherein t and Z are defined as hereinabove; alkyloxy substituted with a radical of formula

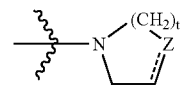

wherein t and Z are defined as hereinabove; mono or di(alkyl) amino wherein alkyl may optionally be substituted with one or two substituents each independently be selected from alkyloxy or Ar or Het or morpholinyl or 2-oxopyrrolidinyl, said $R^2$ being represented by $R^{2a}$, and said compounds being represented by formula (Ia-1), can be prepared by reacting an intermediate of formula (II), wherein $W_1$ represents a suitable leaving group, such as for example halo, e.g. chloro and the like, with H—$R^{2a}$ or with a suitable salt form of $R^{2a}$—H optionally in the presence of a suitable solvent, such as for example an alcohol, e.g. methanol and the like, acetonitrile, and optionally in the presence of a suitable base, such as for example KOH, dipotassium carbonate.

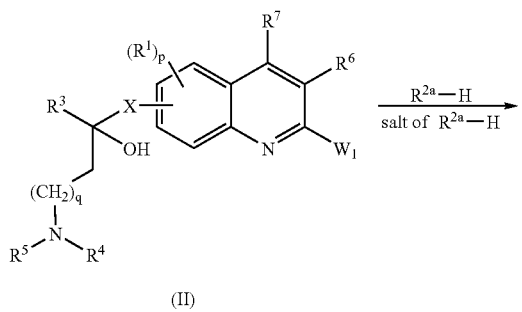

(II)

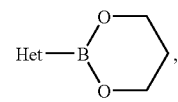

in the presence of a suitable catalyst, such as for example Pd(PPh$_3$)$_4$, a suitable solvent, such as for example dimethylether or an alcohol, e.g. methanol and the like, and a suitable base, such as for example disodium carbonate or dipotassium carbonate.

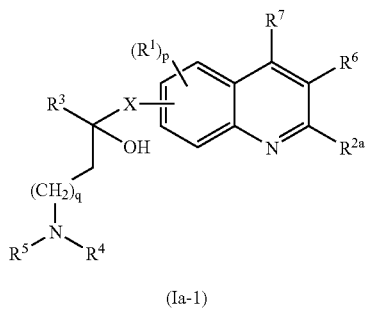

(Ia-1)

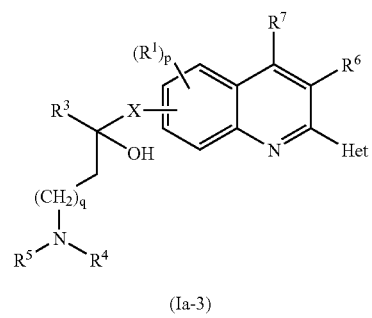

(II)

Compounds of formula (Ia) wherein R$^2$ represents Het or alkyl, said R$^2$ being represented by formula R$^{2b}$ and said compounds being represented by formula (Ia-2), can be prepared by reacting an intermediate of formula (II) with R$^{2b}$—B(OH)$_2$, in the presence of a suitable catalyst, such as for example Pd(PPh$_3$)$_4$, a suitable solvent, such as for example dimethylether or an alcohol e.g. methanol and the like, and a suitable base, such as for example disodium carbonate or dipotassium carbonate.

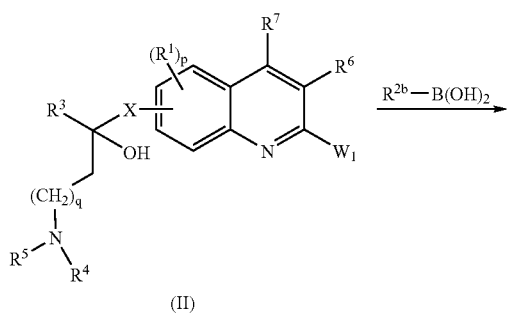

(II)

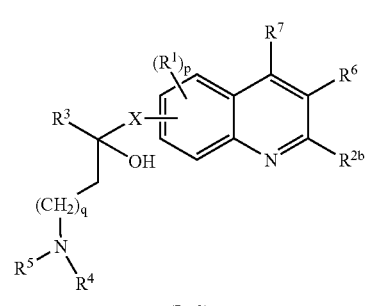

(Ia-3)

Compounds of formula (Ia) wherein X is a direct bond, said intermediates being represented by formula (Ia-4), can be prepared by reacting an intermediate of formula (III) wherein W$_2$ represents a suitable leaving group, such as for example halo, e.g. bromo, chloro and the like, with an intermediate of formula (IV) in the presence of a suitable coupling agent, such as for example n-butyl lithium, secBuLi, and in the presence of a suitable solvent, such as for example tetrahydrofuran, and optionally in the presence of a suitable base, such as for example 2,2,6,6-tetramethylpiperidine, NH(CH$_2$CH$_2$CH$_3$)$_2$, N,N-diisopropylamine or trimethylethylenediamine.

(Ia-2)

Compounds of formula (Ia) wherein R$^2$ represents Het, e.g. pyridyl, said R$^2$ being represented by Het and said intermediates being represented by formula (Ia-3), can be prepared by reacting an intermediate of formula (II) with

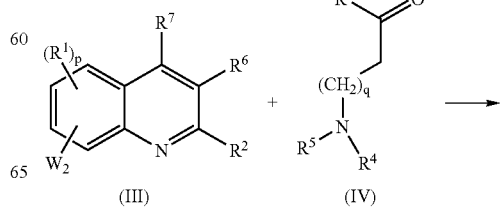

(III)    (IV)

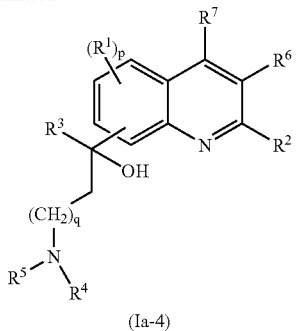

(Ia-4)

Compounds of formula (Ib) wherein $R^9$ represents oxo, can be prepared by reacting an intermediate of formula (II) with a suitable acid, such as for example HCl, in the presence of a suitable solvent, such as for example tetrahydrofuran.

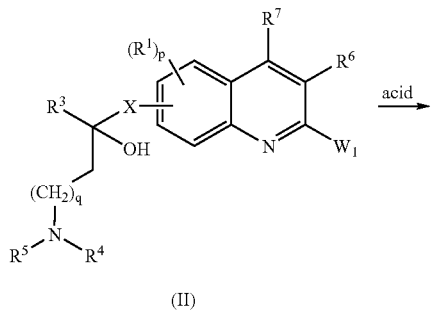

(II)

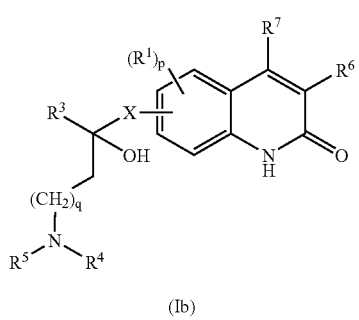

(Ib)

In the above reactions, the obtained compound of formula (Ia) or (Ib) can be isolated, and, if necessary, purified according to methodologies generally known in the art such as, for example, extraction, crystallization, distillation, trituration and chromatography. In case the compound of formula (Ia) or (Ib) crystallizes out, it can be isolated by filtration. Otherwise, crystallization can be caused by the addition of an appropriate solvent, such as for example water, acetonitrile; an alcohol, such as for example methanol, ethanol; and combinations of said solvents. Alternatively, the reaction mixture can also be evaporated to dryness, followed by purification of the residue by chromatography (e.g. reverse phase HPLC, flash chromatography and the like). The reaction mixture can also be purified by chromatography without previously evaporating the solvent The compound of formula (Ia) or (Ib) can also be isolated by evaporation of the solvent followed by recrystallization in an appropriate solvent, such as for example water; acetonitrile; an alcohol such as for example methanol; and combinations of said solvents.

The person skilled in the art will recognize which method should be used, which solvent is the most appropriate to use or it belongs to routine experimentation to find the most suitable isolation method.

The compounds of formula (Ia) or (Ib) may further be prepared by converting compounds of formula (Ia) or (Ib) into each other according to art-known group transformation reactions.

The compounds of formula (Ia) or (Ib) may be converted to the corresponding N-oxide forms following art-known procedures for converting a trivalent nitrogen into its N-oxide form. Said N-oxidation reaction may generally be carried out by reacting the starting material of formula (Ia) or (Ib) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (Ia) wherein $R^1$ represents halo, said compounds being represented by formula (Ia-5), can be converted into a compound of formula (Ia) wherein $R^1$ represents Het, e.g. pyridyl, said compounds being represented by formula (Ia-6), by reaction with

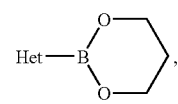

in the presence of a suitable catalyst, such as for example Pd(PPh$_3$)$_4$, a suitable solvent, such as for example dimethylether or an alcohol, e.g. methanol and the like, and a suitable base, such as for example disodium carbonate or dipotassium carbonate.

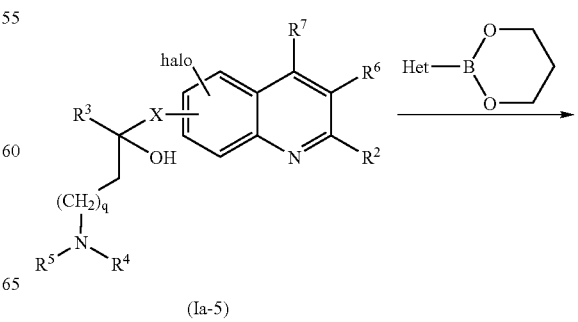

(Ia-5)

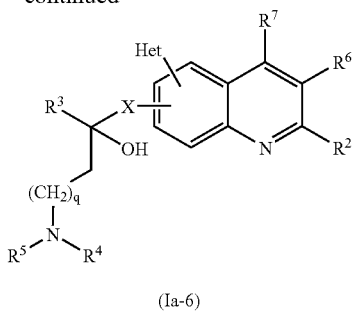

(Ia-6)

Compounds of formula (Ia-5) can also be converted into a compound of formula (Ia) wherein $R^1$ represents methyl, said compound being represented by formula (Ia-7), by reaction with $Sn(CH_3)_4$ in the presence of a suitable catalyst, such as for example $Pd(PPh_3)_4$, a suitable solvent, such as fur example toluene.

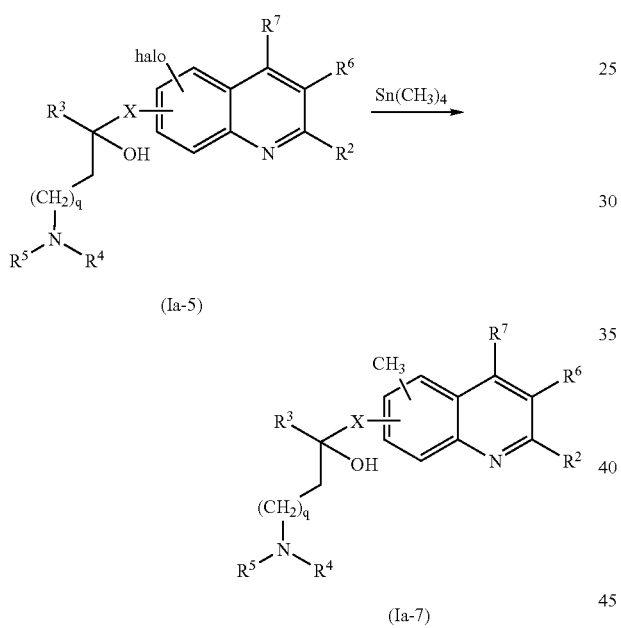

Some of the compounds of formula (I) and some of the intermediates in the present invention may consist of a mixture of stereochemically isomeric forms. Pure stereochemically isomeric forms of said compounds and said intermediates can be obtained by the application of art-known procedures. For example, diastereoisomer can be separated by physical methods such as selective crystallization or chromatographic techniques, e.g. counter current distribution, liquid chromatography and the like methods. Enantiomers can be obtained from racemic by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

It is to be understood that in the above or the following preparations, the reaction products may be isolated from the reaction medium and, if necessary, further purified according to methodologies generally known in the art such as, for example, extraction, crystallization, distillation, trituration and chromatography.

Some of the intermediates and starting materials are known compounds and may be commercially available or may be prepared according to art-known procedures.

Intermediates of formula (II) wherein X is a direct bond, such intermediates being represented by formula (II-a), can be prepared by reacting an intermediate of formula (V) wherein $W_1$ is as defined hereinabove, with an intermediate of formula (IV) in the presence of a suitable coupling agent, such as nBuLi, secBuLi, and in the presence of a suitable solvent, such as for example tetrahydrofuran, and a suitable base, such as for example 2,2,6,6-tetramethylpiperidine, $NH(CH_2CH_2CH_3)_2$, N,N-diisopropylamine or trimethylethylenediamine.

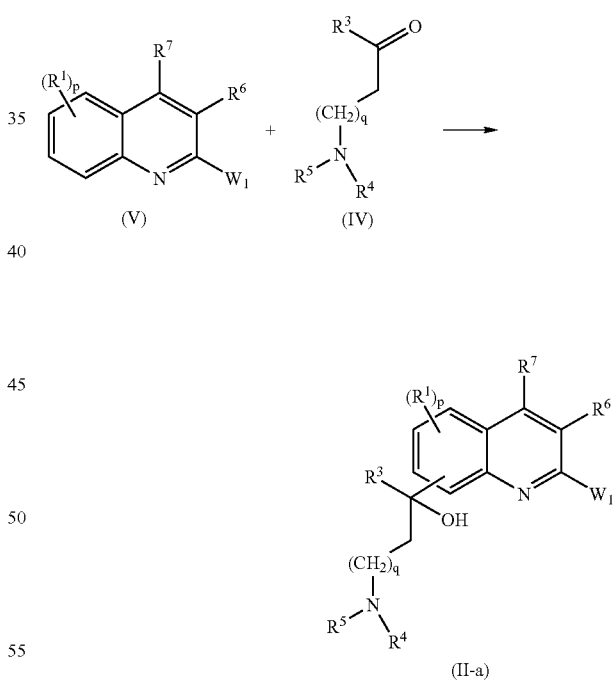

Intermediates of formula (II) wherein X represents $CH_2$, said intermediates being represented by formula (II-b), can be prepared by reacting an intermediate of formula (VI) with an intermediate of formula (IV) in the presence of a suitable coupling agent, such as nBuLi, secBuLi, and in the presence of a suitable solvent, such as for example tetrahydrofuran, and a suitable base, such as for example 2,2,6,6-tetramethylpiperidine, $NH(CH_2CH_2CH_3)_2$, N,N-diisopropylamine or trimethylethylenediamine.

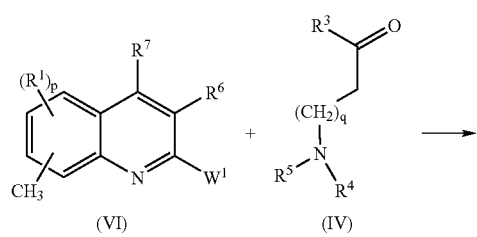

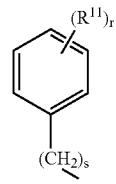

wherein s is an integer equal to 1 and $W_1$ is chloro, said intermediates being represented by formula (V-b) may be prepared according to the following reaction scheme (1):

Scheme 1

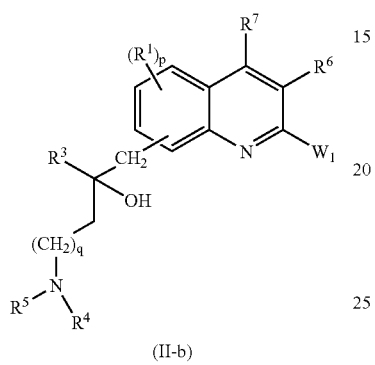

Intermediates of formula (II) wherein $R^1$ is hydrogen, said intermediates being represented by formula (II-c), can be prepared by reacting an intermediate of formula (V) wherein $R^1$ is halo, said intermediates being represented by formula (V-a), with an intermediate of formula (IV), in the presence of a suitable strong base, such as for example nBuLi, secBuLi, and in the presence of a suitable solvent, such as for example tetrahydrofuran.

wherein all variables are defined as in Formula (Ia). Reaction scheme (1) comprises step (a) in which an appropriately substituted aniline is reacted with an appropriate acylchloride such as 3-phenylpropionyl chloride, 3-fluorobenzenepropionyl chloride or p-chlorobenzenepropionyl chloride, in the presence of a suitable base, such as triethylamine and a suitable reaction-inert solvent, such as methylene chloride or ethylene dichloride. The reaction may conveniently be carried out at a temperature ranging between room temperature and reflux temperature. In a next step (b) the adduct obtained in step (a) is reacted with phosphoryl chloride ($POCl_3$) in the presence of a suitable solvent, such as for example N,N-dimethylformamide (Vilsmeier-Haack formylation followed by cyclization). The reaction may conveniently be carried out at a m ranging between room temperature and reflux temperature.

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC. Typically, compounds of Formula (Ia) and (Ib) may be separated into their isomeric forms.

The intermediates of formula (V) are compounds that are either commercially available or may be prepared according to conventional reaction procedures generally known in the art. For example, intermediates of formula (V) wherein $R^7$ is hydrogen, $R^6$ is a radical of formula Intermediates of formula (V-a) wherein WI represents chloro, said intermediates being represented by formula (V-a-1), can be prepared by reacting an intermediate of formula (VII) with $POCl_3$.

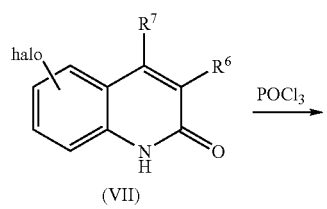

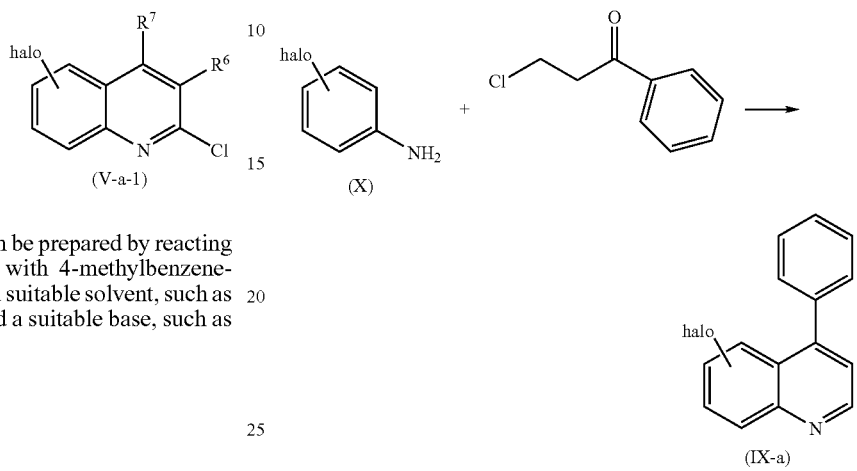

Intermediates of formula (VII) can be prepared by reacting an intermediate of formula (VIII) with 4-methylbenzenesulfonyl chloride in the presence of a suitable solvent, such as fur example methylene chloride, and a suitable base, such as for example dipotassium carbonate.

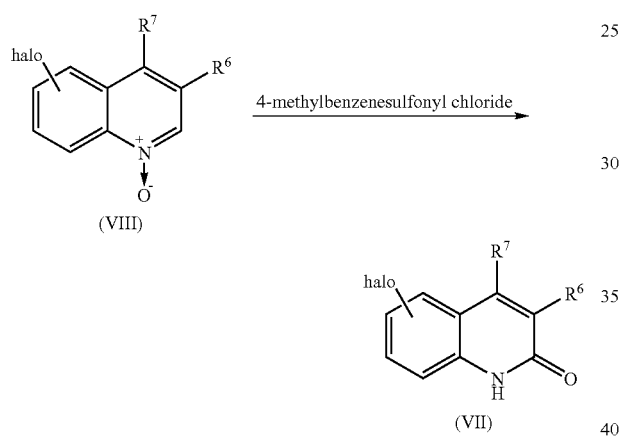

Intermediates of formula (VIII) can be prepared by reacting an intermediate of formula (IX) with a suitable oxidizing agent, such as for example 3-chlorobenzenecarboperoxoic acid, in the presence of a suitable solvent, such as for example methylene chloride.

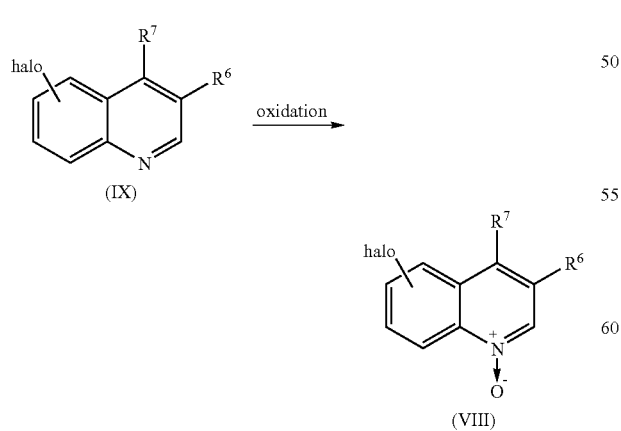

Intermediates of formula (IX) wherein $R^6$ is hydrogen and $R^7$ is phenyl, said intermediates being represented by formula (IX-a), can be prepared by reacting an intermediate of formula (X) with 3-chloro-1-phenyl-1-propanone in the presence of a suitable acid, such as for example hydrochloric acid, iron chloride hexahydrate, zinc chloride and a suitable solvent, such as for example diethyl ether and a suitable alcohol, e.g. ethanol.

Intermediates of formula (IX) wherein $R^7$ is hydrogen and $R^6$ is a radical of formula

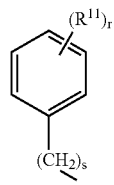

wherein s is an integer equal to 1, said intermediates being represented by formula (IX-b), can be prepared by reacting an intermediate of formula (XI) in the presence of diphenyl ether.

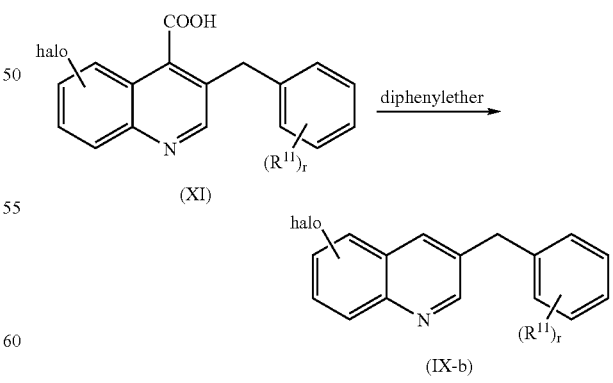

Intermediates of formula (XI) can be prepared by reacting an intermediate of formula (XII) with an intermediate of formula (XIII) in the presence of a suitable base, such as for example sodium hydroxide.

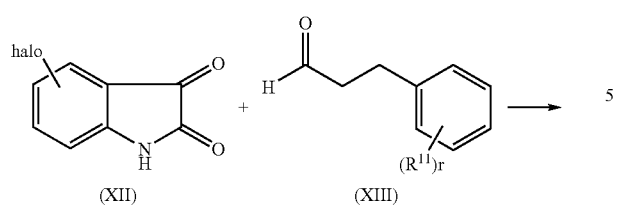

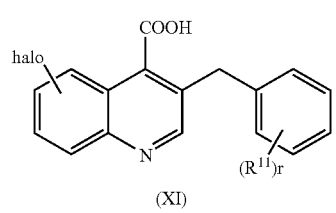

Intermediates of formula (IV) are compounds that are either commercially available or may be prepared according to conventional reaction procedures generally known in the art For example, intermediate compounds of Formula (IV) wherein q is equal to 1, said intermediates being represented by formula (IV-a), can be prepared according to the following reaction scheme (2):

Scheme 2

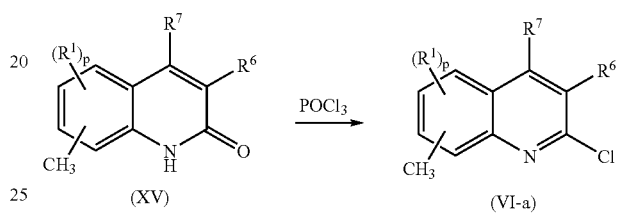

Reaction scheme (2) comprises step (a) in which an appropriately $R^3$ is reacted by Friedel-Craft reaction with an appropriate acylchloride such as 3-chloropropionyl chloride or 4-chlorobutyl chloride, in the presence of a suitable Lewis acid, such as $AlCl_3$, $FeCl_3$, $SnCl_4$, $TiCl_4$ or $ZnCl_2$ and a suitable reaction-inert solvent, such as methylene chloride or ethylene dichloride. The reaction may conveniently be carried out at a temperature ranging between room temperature and reflux temperature. In a next step (b) an amino group (e.g. —$NR^4R^5$) is introduced by reacting the intermediate compound obtained in step (a) with an appropriate amine.

Intermediates of formula (IV-a) can also be prepared by reacting an intermediate of formula (XIV) with HC(=O)H and a suitable amino group $HNR^4R^5$, such as for example $NH(CH_3)_2 \cdot HCl$ in the presence of a suitable solvent, such as for example an alcohol, e.g. methanol, ethanol and the like, and a suitable acid, such as for example hydrochloric acid.

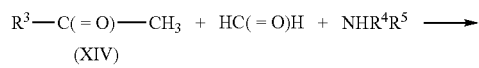

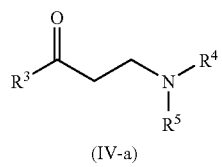

Intermediates of formula (VI) wherein $W_1$ represents chloro, said intermediates being represented by formula (VI-a) can be prepared by reacting an intermediate of formula (XV) with $POCl_3$ in the presence of benzyltriethylammonium chloride (Phase transfer agent) and a suitable solvent, such as for example acetonitrile.

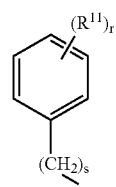

Intermediates of formula (XV) wherein $R^6$ represents a radical of formula wherein s is an integer equal to 1, said intermediates being represented by formula (XV-a), can be prepared by reacting an intermediate of formula X) with $NH_2$—$NH_2$ in the presence of a suitable base, such as for example potassium hydroxide and a suitable solvent, such as for example 1,2-ethanediol.

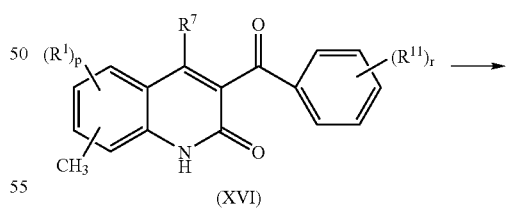

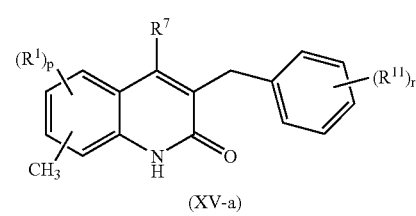

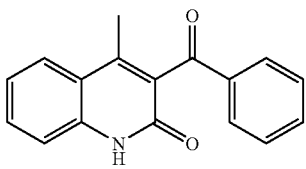

which is an intermediate of formula (XVI) can be prepared by reacting 1-(2-aminophenyl)ethanone and β-oxobenzenepropanoic acid ethyl ester.

Intermediates of formula (III) wherein $R^2$ represents $C_{1-6}$alkyloxy said intermediates being represented by formula (III-a), can be prepared by reacting an intermediate of formula (XVII) with the appropriate $C_{1-6}$alkyl— salt in the presence of a suitable solvent, such as for example the corresponding $C_{1-6}$alkyl OH.

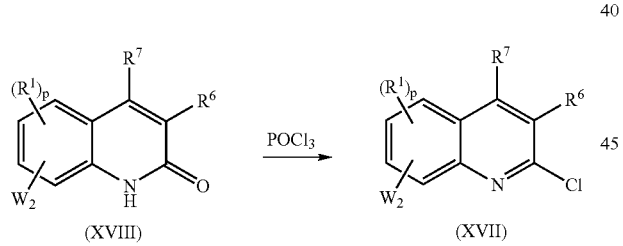

Intermediates of formula (XVII) can be prepared by reacting an intermediate of formula (XVIII) with $POCl_3$.

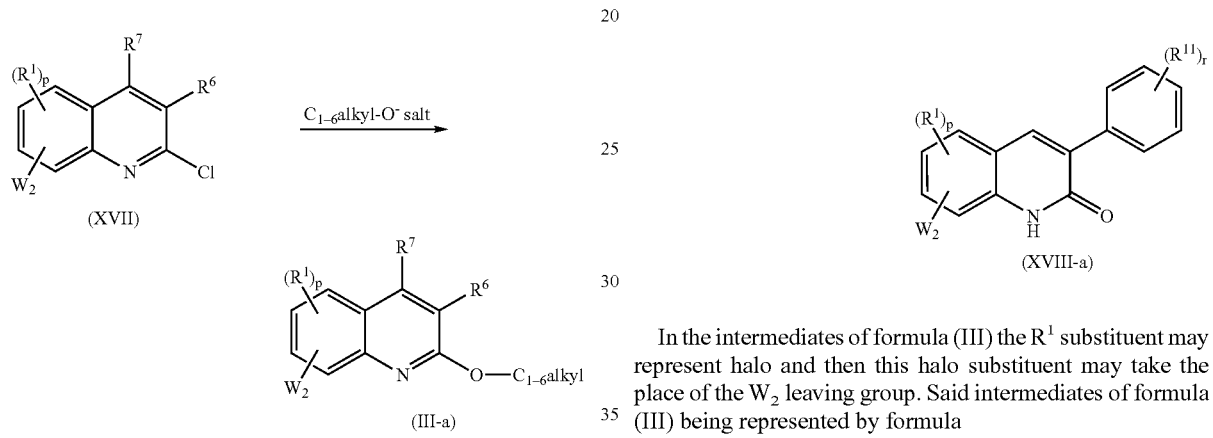

Intermediates of formula (XVIII) wherein $R^7$ is hydrogen and $R^6$ represents a radical of formula

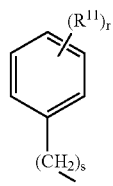

wherein s is an integer equal to 0, said intermediates being represented by formula (XVIII-a), can be prepared by cyclization of an intermediate of formula (XIX) in the presence of $AlCl_3$ and a suitable solvent, such as for example chlorobenzene.

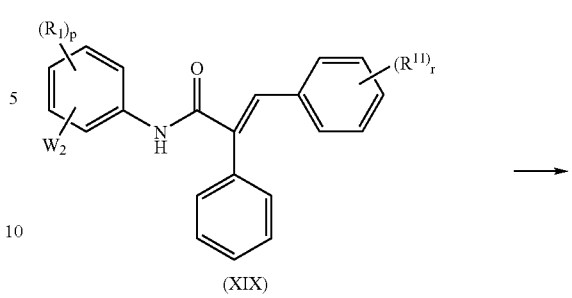

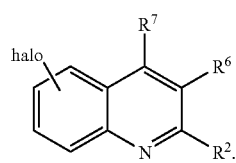

In the intermediates of formula (III) the $R^1$ substituent may represent halo and then this halo substituent may take the place of the $W_2$ leaving group. Said intermediates of formula (III) being represented by formula

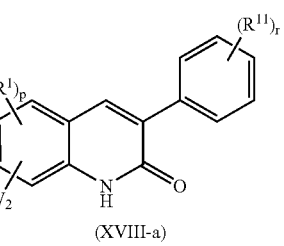

The following examples illustrate the present invention without being limited thereto.

EXPERIMENTAL PART

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The isolation method is described in detail below.

Hereinafter, the term 'M.P.' means melting point, 'DIPE' means diisopropyl ether, 'DMF' means N,N-dimethylformamide, 'THF' means tetrahydrofuran, 'EtOAc' means ethyl acetate, 'DCM' means dichloromethane.

A. Preparation of the Intermediates

Example A1

Preparation of Intermediate 1

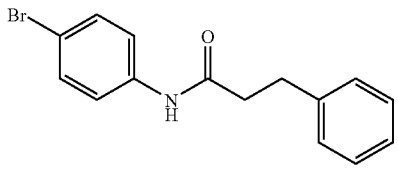

Benzenepropanoyl chloride (0.488 mol) was added dropwise at room temperature to a solution of 4-bromo benzenamine (0.407 mol) in Et₃N (70 ml) and DCM (700 ml) and the mixture was stirred at room temperature overnight. The mixture was poured out into water and concentrated NH₄OH, and extracted with DCM. The organic layer was dried (MgSO₄), filtered, and the solvent was evaporated. The residue was crystallized from diethyl ether. The residue (119.67 g) was taken up in DCM and washed with HCl 1N. The organic layer was dried (MgSO₄), filtered, and the solvent was evaporated, yielding 107.67 g of intermediate 1 (87%).

Example A2

Preparation of Intermediate 2

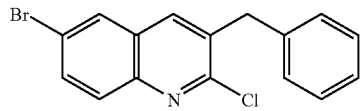

Phosphoric trichloride (1.225 mol) was added dropwise at 10° C. to DMF (0.525 mol). Then intermediate 1 (0.175 mol) was added at room temperature. The mixture was stirred overnight at 80° C., poured out on ice and extracted with DCM. The organic layer was dried (MgSO₄), filtered, and the solvent was evaporated. The product was used without further purification, yielding 77.62 g of intermediate 2 (67%).

Example A3 a) Preparation of Intermediate 3

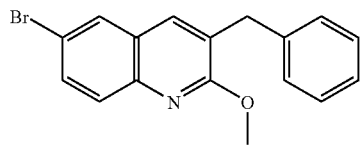

A mixture of intermediate 2 (0.233 mol) in a 30% MeONa in MeOH solution (222.32 ml) and MeOH (776 ml) was stirred and refluxed overnight, then poured out on ice and extracted with DCM. The organic layer was separated, dried (MgSO₄), filtered and the solvent was evaporated. The residue was purified by column chromatography over silica gel (eluent: DCM/cyclohexane 20/80 and then 100/0; 20-45 μm). The pure fractions were collected and the solvent was evaporated, yielding 25 g of intermediate 3 (33%).

The following intermediate was prepared according to the method described above.

intermediate 29

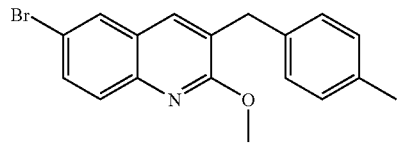

b) Preparation of Intermediate 4

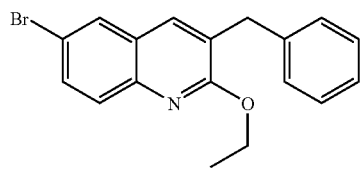

A mixture of intermediate 2 (0.045 mol) in a 21% EtONa in EtOH solution (50 ml) and EtOH (150 ml) was stirred and refluxed for 12 hours. The mixture was poured out on ice and extracted with DCM. The organic layer was separated, dried (MgSO₄), filtered and the solvent was evaporated, yielding 15.2 g of intermediate 4 (98%).

Example A4 a) Preparation of Intermediate 5

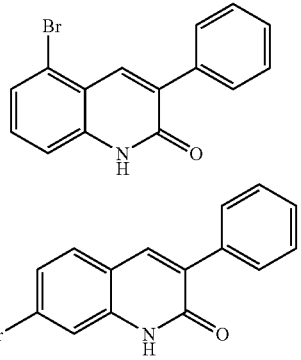

Aluminum chloride (1.31 mol) was added at room temperature to a mixture of N-(3-bromophenyl)-α-(phenylmethylene)benzeneacetamide (0.1311 mol) in chlorobenzene (500 ml). The mixture was stirred and refluxed for 3 hours, then cooled to room temperature, poured out into ice water and filtered. The filtrate was washed with H₂O, then with cyclohexane and dried, yielding 35.5 g of intermediate 5 (95%).

b) Preparation of Intermediate 6 and Intermediate 7 intermediate 6

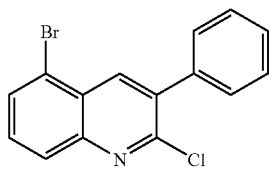

33
-continued intermediate 7

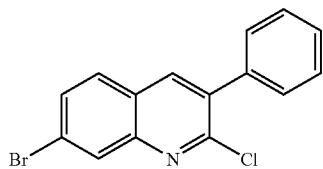

A mixture of intermediate 5 (0.2815 mol) in phosphoric trichloride (320 ml) was stirred and refluxed for 1 hour, then cooled to room temperature and the solvent was evaporated till dryness. The residue was taken up in $H_2O$. The mixture was extracted with DCM. The organic layer was separated, dried ($MgSO_4$), filtered, and the solvent was evaporated till dryness. The residue (58.2 g) was purified by column chromatography over silica gel (eluent toluene/cyclohexane 80/20; 15-35 μm). Two fractions were collected and the solvent was evaporated, yielding 21 g of intermediate 6 and 34.5 g of intermediate 7.

c) Preparation of Intermediate 8

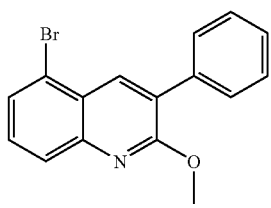

A mixture of intermediate 6 (0.0659 mol) and a 30% MeONa in MeOH solution (0.329 mol) in MeOH (300 ml) was stirred and refluxed for 2 days, then cooled to room temperature, poured out into ice water and filtered. The filtrate was washed with $H_2O$ and dried, yielding 19 g of intermediate 8 (92%).

Example A5 a) Preparation of Intermediate 9

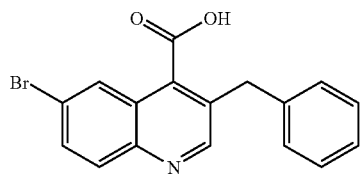

A mixture of 5-bromo-1H-indole-2,3-dione (0.28 mol) in 3N NaOH (650 ml) was stirred and heated at 80° C. for 30 minutes, then cooled to room temperature. Benzenepropanal (0.28 mol) was added and the mixture was stirred and refluxed overnight. The mixture was allowed to cool to room temperature and acidified till pH 5 with HOAc. The precipitate was filtered off, washed with $H_2O$ and dried (vacuum), yielding 50 g of intermediate 9 (52%).

34 b) Preparation of Intermediate 10

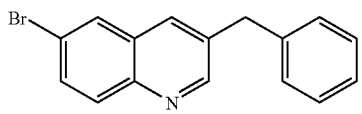

A mixture of intermediate 9 (0.035 mol) in 1,1'-oxybisbenzene (100 ml) was stir and heated at 300° C. for 8 hours, then allowed to cool to room temperature. This procedure was carried out four times. The four mixtures were combined and then purified by column chromatography over silica gel (eluent: DCM/MeOH 100/0, then 99/1). The pure fractions were collected and the solvent was evaporated, yielding 25.6 g of intermediate 10 (61%).

Example A6 a) Preparation of Intermediate 11

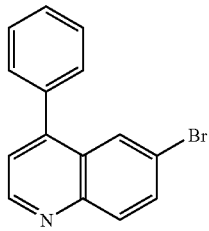

HCl/diethyl ether (30 ml) was added to a solution of 4-bromobenzenamine (0.139 mol) in EtOH (250 ml) and the mixture was stirred for 30 minutes. Iron chloride hexahydrate (0.237 mol) and then zinc chloride (0.014 mol) were added and the mixture was stirred at 80° C. for 30 minutes. 3-Chloro-1-phenyl-1-propanone (0.146 mol) was added and the mixture was stirred at 80° C. for one night. The mixture was poured into water and extracted with EtOAc. The organic layer was washed with water, then with $K_2CO_3$ 10%, dried ($MgSO_4$), filtered off and evaporated. The residue (25 g) was purified by column chromatography over silica gel (eluent: DCM/MeOH 100/0 and then 97/3) (35-70 μm). The pure fractions were collected and evaporated, yielding 17.5 g of intermediate 11 (44%).

b) Preparation of Intermediate 12

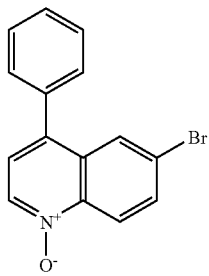

3-Chlorobenzenecarboperoxoic acid (0.12 mol) was added portionwise at room temperature to a solution of intermediate 11 (0.0598 mol) in DCM (200 ml) and the mixture was stirred at room temperature for one night. $K_2CO_3$ 100% was added, the organic layer was decanted, dried ($MgSO_4$), filtered off and evaporated till a volume of 150 ml of intermediate 12 was left.

c) Preparation of Intermediate 13

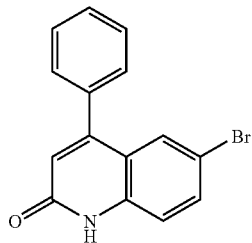

4-Methylbenzenesulfonyl chloride (0.075 mol) was added portionwise at room temperature to a solution of intermediate 12 (0.0598 mol) in a 10% K$_2$CO$_3$ solution (150 ml) and DCM (150 ml) and the mixture was stirred at room temperature for one night. Diethyl ether was added and filtered off. The precipitate was washed with diethyl ether and evaporated till dryness, yielding 14 g of intermediate 13 (78%).

d) Preparation of Intermediate 14

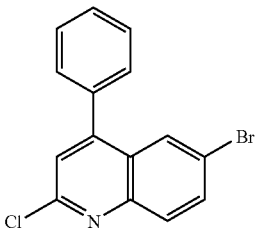

A mixture of intermediate 13 (0.047 mol) in phosphoric trichloride (150 ml) was stirred and refluxed for 48 hours. The mixture was evaporated, the residue was taken up in NH$_4$OH and exacted with DCM. The organic layer was dried (MgSO$_4$), filtered off and evaporated, yielding 13 g of intermediate 14 (87%).

Example A7 a) Preparation of Intermediate 15

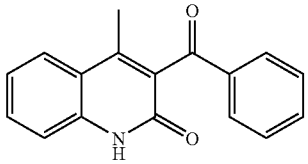

A mixture of 1-(2-aminophenyl)ethanone (0.37 mol) and β-oxobenzenepropanoic acid ethyl ester (1.48 mol) was stirred at 180° C. overnight. The mixture was brought to room temperature. The precipitate was filtered, washed with diethyl ether and dried. The residue was crystallized from DIPE. The precipitate was filtered off and dried, yielding 56.6 g of intermediate 15 (58%).

b) Preparation of Intermediate 16

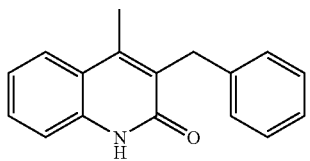

A mixture of intermediate 15 (0.076 mol) and hydrazine (0.76 mol) in 1,2-ethanediol (240 ml) was stirred at 100° C. for 1 hour. KOH (0.266 mol) was added. The mixture was stirred at 180° C. overnight. H$_2$O was added. The mixture was acidified and extracted with DCM. The organic layer was separated, dried (MgSO$_4$), filtered, and the solvent was evaporated. The residue (12.05 g) was crystallized from DIPE. The precipitate was filtered off and dried, yielding 4.74 g of intermediate 16.

c) Preparation of Intermediate 17

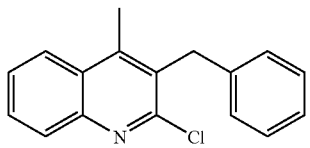

Phosphoric trichloride (0.057 mol) was added slowly at 80° C. to a mixture of intermediate 16 (0.019 mol) and benzyltriethylammonium chloride (0.0532 mol) in acetonitrile (50 ml). The mixture was stirred overnight. The solvent was evaporated. The mixture was poured out into ice and Na$_2$CO$_3$ 10% and extracted with DCM. The organic layer was separated, dried (MgSO$_4$), filtered, and the solvent was evaporated, yielding 4.08 g of intermediate 17.

Example A8 a) Preparation of Intermediate 18 and Intermediate 19

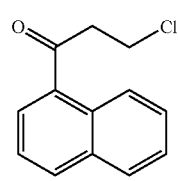
intermediate 18

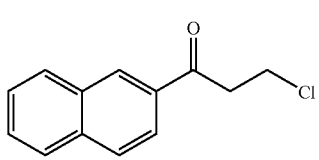
intermediate 19

A mixture of aluminium chloride (0.257 mol) and 3-chloropropanoyl chloride (0.234 mol) in 1,2-chloroethane (100 ml) was stirred at 0° C. A solution of naphthalene (0.234 mol) in 1,2-dichloroethane (100 ml) was added. The mixture was stirred at 0° C. for 1 hour and poured out into ice water. The organic layer was separated, dried (MgSO$_4$), filtered, and the solvent was evaporated. The residue (56 g) was purified by column chromatography over silica gel (eluent: cyclohexane/DCM 60/40; 20-45 μm). Two fractions were collected and the solvent was evaporated, yielding 2 fractions, 31 g of faction 1 as intermediate 18 (61%) and 14 g of fraction 2. Fraction 2 was taken up in DIPE, then the resulting precipitate was filtered off and dried, yielding 8.2 g of intermediate 19.

b) Preparation of Intermediate 20

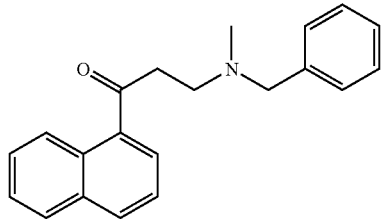

A mixture of intermediate 18 (0.0137 mol), N-methylbenzenemethanamine (0.015 mol) and K$_2$CO$_3$ (2 g) in acetonitrile (100 ml) was stirred at 80° C. for 2 hours. H$_2$O was added. The mixture was extracted with DCM. The organic layer was separated, dried (MgSO$_4$), filtered, and the solvent was evaporated, yielding 4.2 g of intermediate 20 (100%).

Example A9

Preparation of Intermediate 21

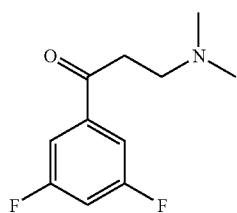

A mixture of 1-(3,5-difluorophenyl)ethanone (0.013 mol), formaldehyde (0.05 mol) and N-methylmethaiimine hydrochloride (0.052 mol) in concentrated HCl (0.1 ml) in EtOH (20 ml) was stirred at 80° C. for 20 hours, then cooled to room temperature. The solvent was evaporated till dryness. The residue was taken up in HCl 3N. The mixture was washed with diethyl ether, basified with K$_2$CO$_3$ and extracted with diethyl ether. The organic layer was separated, dried (MgSO$_4$), filtered, and the solvent was evaporated, yielding 2 g of intermediate 21.

Example A10 a) Preparation of Intermediate 22 and Intermediate 23 intermediate 22

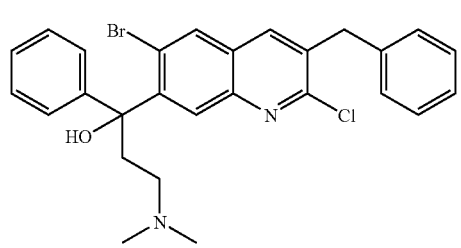

intermediate 23

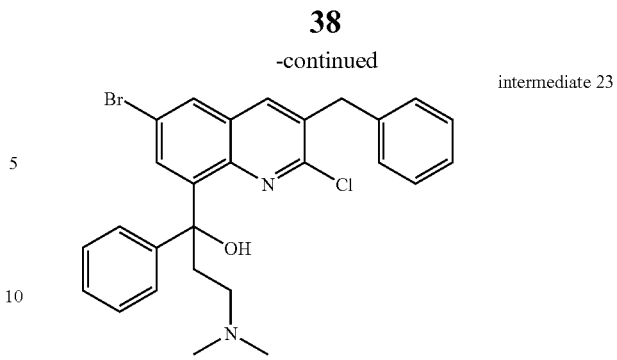

1.6M Butyllithium (0.12 mol) was added dropwise at –10° C. under N$_2$ flow to a solution of 2,2,6,6-tetramethylpiperidine (0.12 mol) in TTF (200 ml). The mixture was stirred at –10° C. for 20 minutes and then cooled to –700° C. A mixture of intermediate 2 (0.1 mol) in THF (100 ml) was added. The mixture was stirred at –70° C. for 45 minutes. A solution of 3-(dimethylamino)-1-phenyl-1-propanone (0.1 mol) in THF (100 ml) was added. The mixture was stirred at –70° C. for 1 hour, brought to –50° C. and hydrolysed. H$_2$O (100 ml) was added at –50° C. The mixture was stirred at room temperature for 30 minutes and extracted with EtOAc. The organic layer was separated, dried (MgSO$_4$), filtered and the solvent was evaporated. The residue was taken up in EtOAc. The precipitate was filtered off, washed with EtOAc and diethyl ether and dried in vacuo, yielding 4 g of intermediate 23 (8%). The mother layer was evaporated. The residue (26 g) was purified by column chromatography over silica gel (eluent: DCM/MeOH/NH$_4$OH 97/3/0.1; 15-40 µm). The desired fractions were collected and the solvent was evaporated. The residue was crystallized from diethyl ether. The precipitate was filtered off and dried, yielding 1 g of intermediate 22.

The following intermediates were prepared according to the method described above.

intermediate 30

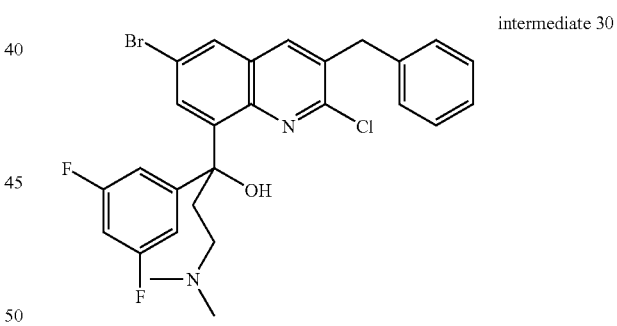

intermediate 31

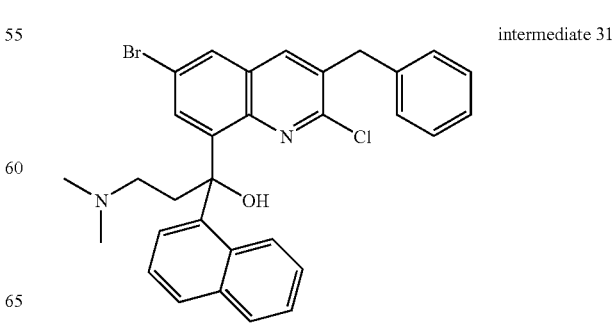

b) Preparation of Intermediate 24

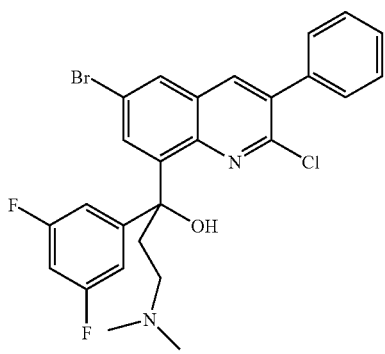

1.6M Butyllithium (0.0094 mol) was added dropwise at −20° C. to a mixture of 2,2,6,6-tetramethylpiperidine (0.0094 mol) in THF (20 ml) under $N_2$ flow. The mixture was stirred at −20° C. for 20 minutes, then cooled to −70° C. A solution of 6-bromo-2-chloro-3-phenylquinoline (0.0062 mol) in THF (40 ml) was added. The mixture was stirred at −70° C. for 1 hour. A solution of intermediate 21 (0.0094 mol) in THF (25 ml) was added. The mix was stirred from −70° C. to room temperature for 18 hours. $H_2O$ and EtOAc were added The organic layer was washed with saturated NaCl, dried ($MgSO_4$), filtered, and the solvent was evaporated. The residue (4.3 g) was purified by column chromatography over silica gel (eluent: DCM/MeOH/$NH_4OH$ 97/3/0.1; 10 μm). The pure fractions were collected and the solvent was evaporated, yielding 0.77 g of intermediate 24 (23%).

The following intermediates were prepared according to the method described above.

intermediate 32

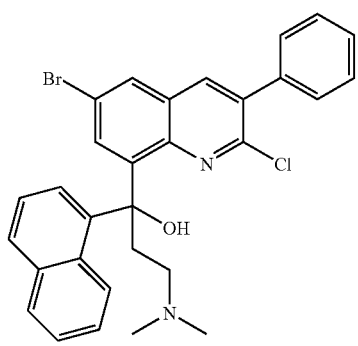

intermediate 34

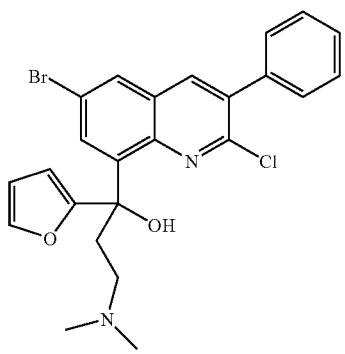

c) Preparation of Intermediate 28

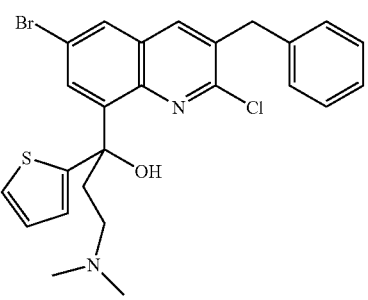

1.6M Butyllithium (0.029 mol) was added at −10° C. to a solution of N-propyl-1-propanamine (0.029 mol) in TH (50 ml) under $N_2$ flow. The mixture was stirred for 20 minutes, then cooled to −70° C. A solution of intermediate 2 (0.024 mol) in THF (30 ml) was added. The mixture was stirred at −70° C. for 1 hour. A solution of 3-(dimethylamino)-1-(2-thienyl)-1-propanone (0.029 mol) in THF (20 ml) was added. The mixture was stirred at −70° C. for 1 hour, then brought to −20° C. and extracted with EtOAc. The organic layer was separated, dried ($MgSO_4$), filtered, and the solvent was evaporated. The residue was purified by column chromatography over silica gel (eluent: DCM/MeOH/$NH_4OH$ 96/4/0.1; 20-45 μm). The pure fractions were collected and the solvent was evaporated. The residue (4.65 g) was crystallized from DIPE. The precipitate was filtered off and dried, yielding 2.7 g of intermediate 28 (M.P.: 168° C.). The mother layer was evaporated, yielding another 1.7 g of intermediate 28.

d) Preparation of Intermediate 25

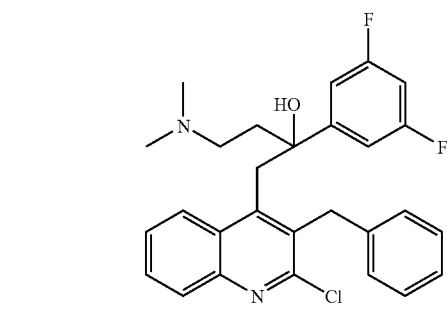

1.6M Butyllithium (0.0112 mol) was added dropwise at −20° C. to a solution of N-(1-methylethyl)-2-propanamine (0.0112 mol) in THF (20 ml) under $N_2$ flow. The mixture was stirred at −20° C. for 30 minutes, then cooled to −70° C. A solution of intermediate 17 (0.0094 mol) in THF (20 ml) was added. The mixture was stirred for 45 minutes. A solution of intermediate 21 (0.0112 mol) in THF (10 ml) was added. The mixture was stirred at −70° C. for 2 hours, poured out into $H_2O$ at −30° C. and extracted with EtOAc. The organic layer was separated, dried ($MgSO_4$), filtered, and the solvent was evaporated. The residue (4 g) was purified by column chromatography over silica gel (eluent: DCM/MeOH 98/2; 15-40 μm). The pure fractions were collected and the solvent was evaporated. The residue (3 g) was crystallized from DIPE. The precipitate was filtered off and dried, yielding 1.94 g of intermediate 25 (43%) (M.P.: 140° C.).

e) Preparation of Intermediate 26

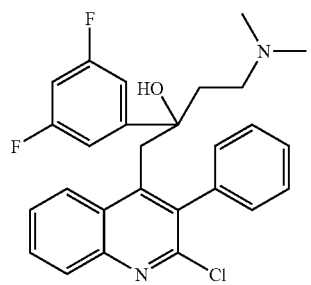

1.6M Butyllithium (0.013 mol) was added dropwise at −30° C. to a mixture of N-(1-methylethyl)-2-propanamine (0.013 mol) in THF (20 ml) under $N_2$ flow. The mixture stirred at −20° C. for 30 minutes, then cooled to −70° C. A solution of 2-chloro4-methyl-3-phenylquinoline (0.011 mol) in THF (20 ml) was added. The mixture was stirred for 45 minutes. A solution of intermediate 21 (0.013 mol) in THF (10 ml) was added. The mixture was stirred at −70° C. for 2 hours, poured out into $H_2O$ and extracted with EtOAc. The organic layer was separated, dried ($MgSO_4$), filtered, and the solvent was evaporated. The residue (5 g) was purified by column chromatography over silica gel (eluent: DCM/MeOH 98/2; 15-40 μm). The pure fractions were collected and the solvent was evaporated, yielding 4 g of intermediate 26 (78%).

f) Preparation of Intermediate 27

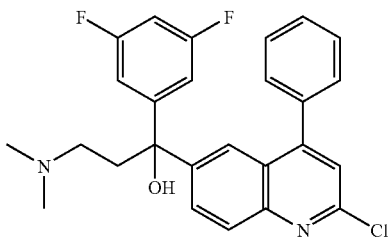

1.6M Butyllithium in hexane (0.0075 mol) was added dropwise at −70° C. to a mixture of intermediate 14 (0.0062 mol) in THF (20 ml) under $N_2$ flow. The mixture was stirred at −70° C. for 1 hour. A solution of intermediate 21 (0.0075 mol) in THF (10 ml) was added at −70° C. The mixture was stirred from −70° C. to room temperature then stirred for 18 hours. $H_2O$ was added. The mixture was extracted with EtOAc. The organic layer was washed with saturated NaCl, dried ($MgSO_4$), filtered and the solvent was evaporated. The residue (3 g) was purified by column chromatography over silica gel (eluent: DCM/MeOH/$NH_4OH$ 97/3/0.1; 15-40 μm).

The pure fractions were collected and the solvent was evaporated, yielding 1.1 g of intermediate 27 (39%).

The following intermediates were prepared according to the method described above.

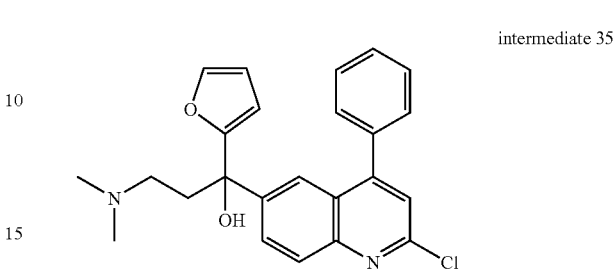

intermediate 35

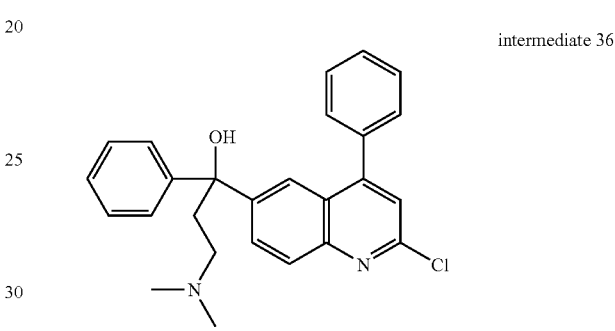

intermediate 36

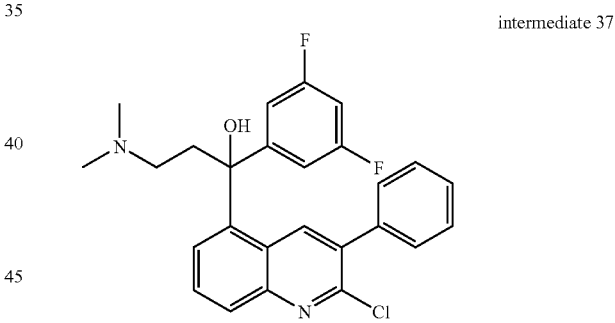

intermediate 37

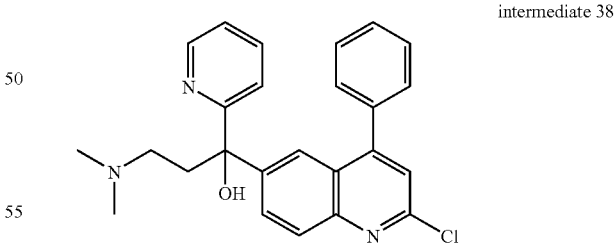

intermediate 38

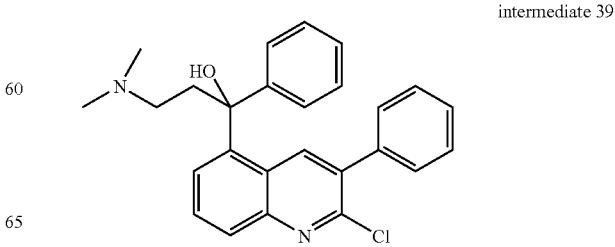

intermediate 39

-continued intermediate 40

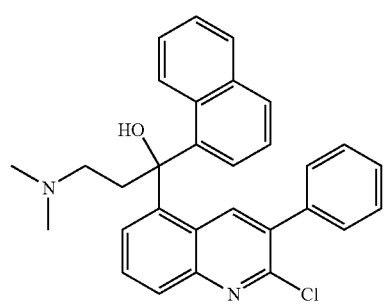

B. Preparation of the Final Compounds

Example B1 a) Preparation of Compound 1

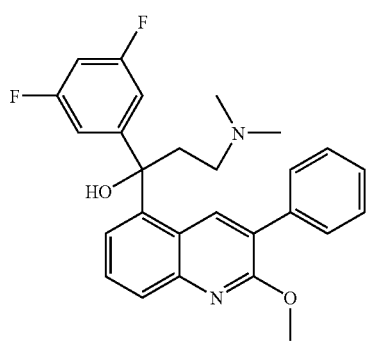

1.6M Butyllithium (0.0019 mol) was added dropwise at −70° C. to a mixture of intermediate 8 (0.0016 mol) in THF (5 ml) under $N_2$ flow. The mixture was stirred at −70° C. for 1 hour. A solution of intermediate 21 (0.0019 mol) in THF (2 ml) was added. $H_2O$ was added. The mixture was exacted with DCM. The organic layer was separated, dried (MgSO$_4$), filtered, and the solvent was evaporated The residue was purified by column chromatography over silica gel (eluent DCM/MeOH/NH$_4$OH 98/2/0.1; 10 μm). The pure fractions were collected and the solvent was evaporated, yielding 0.2 g of compound 1 (28%, MH+: 449).

The following final compounds were prepared according to the method described above.

compound 18

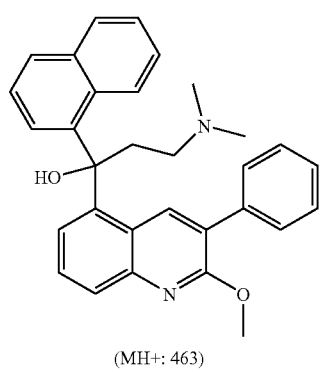

(MH+: 463)

-continued compound 19

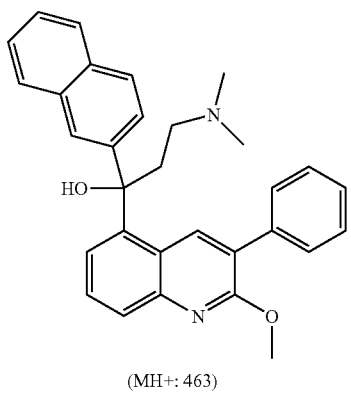

(MH+: 463)

compound 20

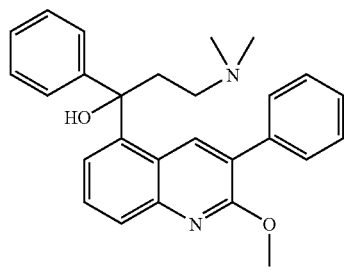

(M. P.: 173° C.)

compound 21

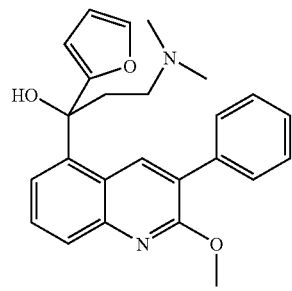

(MH+: 403)

compound 22

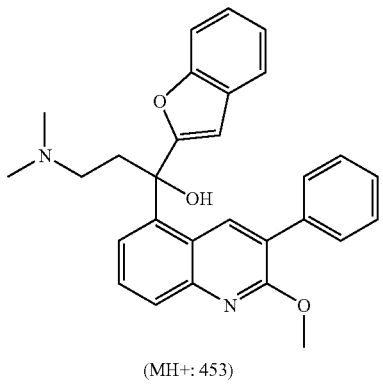

(MH+: 453)

-continued

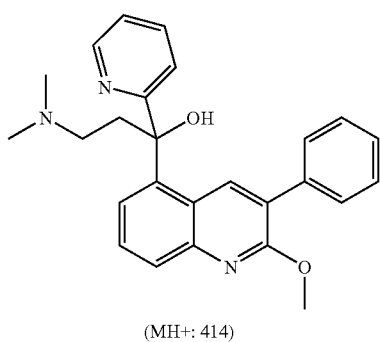
compound 23

(MH+: 414)

b) Preparation of Compound 2

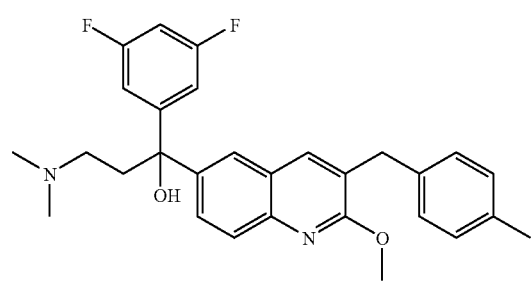

Butyllithium (0.0035 mol) was added dropwise at −20° C. to a solution of N-(1-methylethyl)-2-propanamine (0.0034 mol) in THF (10 ml) under $N_2$ flow. The mixture was stirred at −20° C. for 20 minutes, then cooled to −70° C. A solution of intermediate (0.0029 mol) in THF (10 ml) was added. The mixture was stirred at −70° C. for 2 hours. A solution of intermediate 21 (0.0032 mol) in THF (10 ml) was added at −70° C. The mixture was stirred at −70° C. for 3 hours, poured out into ice water and extracted with DCM. The organic layer was separated, dried ($MgSO_4$), filtered, and the solvent was evaporated. The residue (1.4 g) was purified by column chromatography over silica gel (eluent: DCM/MeOH/$NH_4OH$ 99/1/0.1; 15-40 μm). The desired fraction was collected and the solvent was evaporated. The residue (0.968 g) was purified by column chromatography over silica gel (eluent: DCM/MeOH/$NH_4OH$ 98/2/0.2; 15-40 μm). The pure fractions were collected and the solvent was evaporated. The residue was dried, yielding 0.151 g of compound 2 (11%, oil).

Example B2 a) Preparation of Compound 3

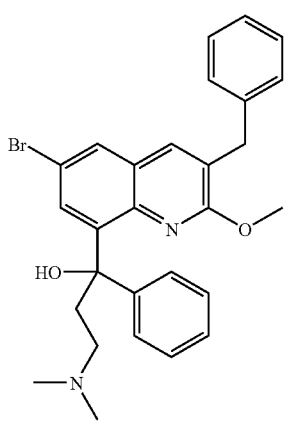

A 30% MeONa solution (2 ml) was added at room temperature to a mixture of intermediate 23 (0.002 mol) in MeOH (2 ml). The mixture was stirred and refluxed overnight, poured out on ice and extracted with DCM. The organic layer was separated, dried ($MgSO_4$), filtered, and the solvent was evaporated The residue (0.62 g) was purified by column chromatography over silica gel (eluent DCM/MeOH/$NH_4OH$ 95/510.5; 15-40 μm). The pure fractions were collected and the solvent was evaporated. The obtained residue (0.39 g) was crystallized from DIPE. The precipitate was filtered off and dried, yielding 0.15 g of compound 3 (M.P.: 66° C.).

The following final compounds were prepared according to the method described above.

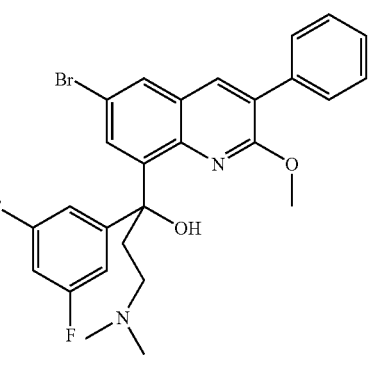
compound 12

(M. P.: 170° C.)

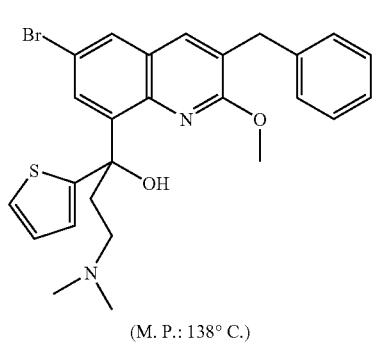
compound 15

(M. P.: 138° C.)

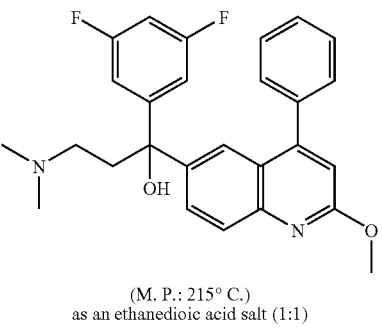
compound 24

(M. P.: 215° C.)
as an ethanedioic acid salt (1:1)

compound 25
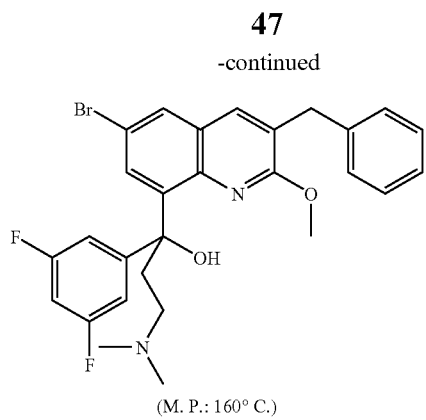
(M. P.: 160° C.)
compound 26
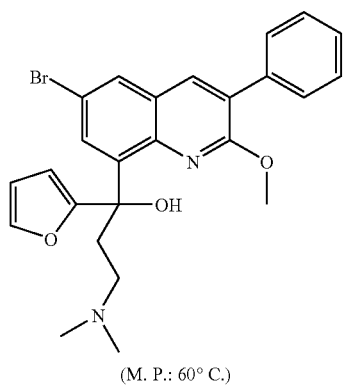
(M. P.: 60° C.)
compound 27
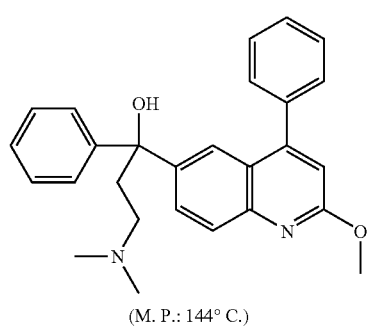
(M. P.: 144° C.)
compound 28
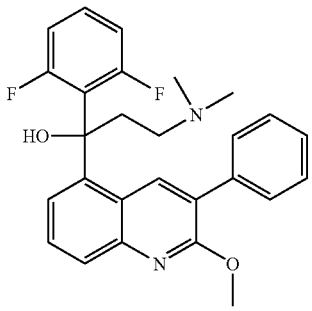
(MH+: 449)
compound 29
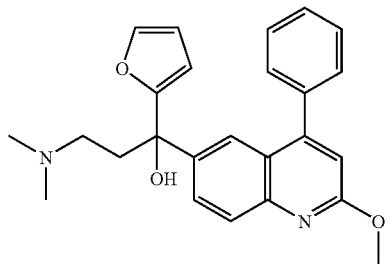
(MH+: 403)
compound 30
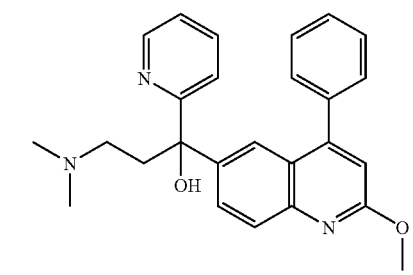
(M. P.: 132° C)
as an ethanedioic acid salt (1:1)
b) Preparation of Compound 4
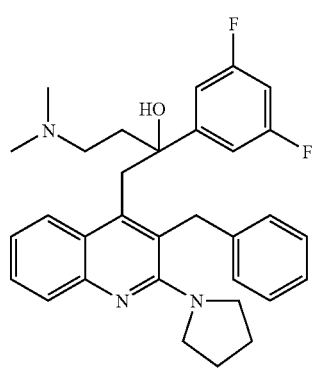

A mixture of intermediate 25 (0.0004 mol) and pyrrolidine (0.0021 mol) was stirred at 90° C. overnight, then poured out into H₂O and extracted with DCM. The organic layer was separated, dried (MgSO₄), filtered, and the solvent was evaporated. The residue (0.18 g) was purified by column chromatography over silica gel (eluent: DCM/MeOH/NH₄OH 98/2/0.1; 10 μm). The desired fraction was collected and the solvent was evaporated, yielding 0.043 g of compound 4 (20%, MH+: 516).

The following final compounds were prepared according to the method described above.

compound 31

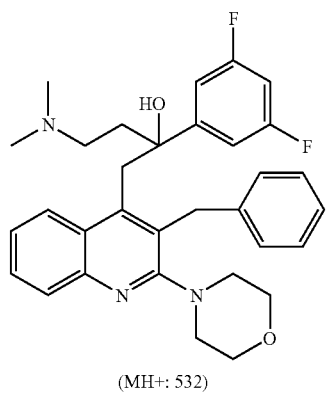

(MH+: 532)

compound 32

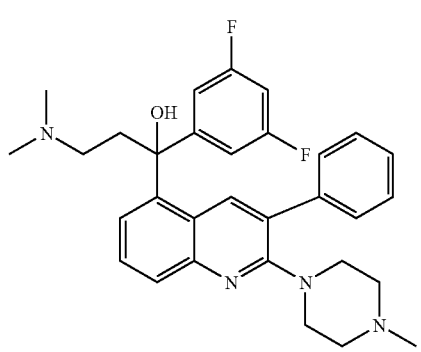

(M. P.: 152° C.)
as an ethanadioic acid salt (1:2)

compound 33

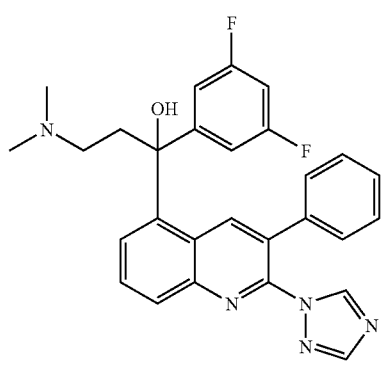

(M. P.: 198° C.)

compound 34

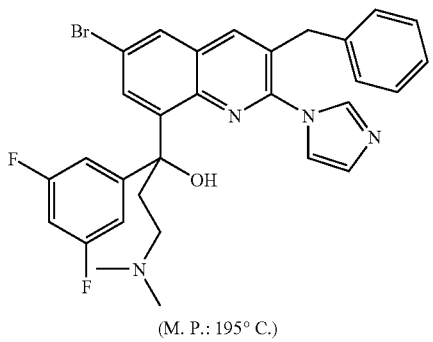

(M. P.: 195° C.)

compound 35

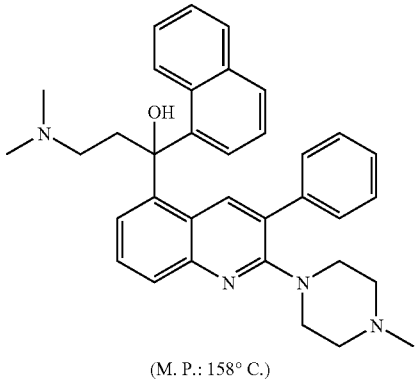

(MH+: 579)

compound 36

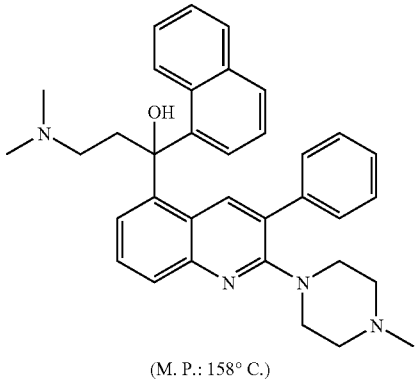

(M. P.: 158° C.)
as an ethanedioic acid salt (1:3)

compound 37

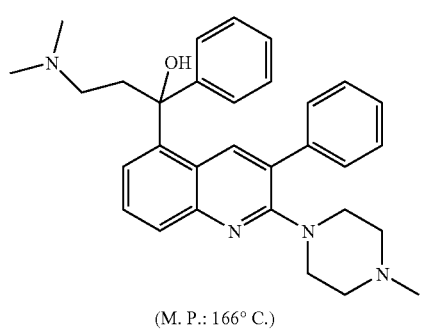

(M. P.: 166° C.)

compound 38

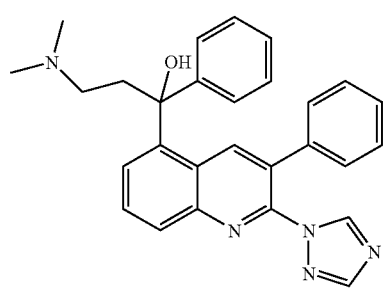

(M. P.: 188° C.)

c) Preparation of Compound 5

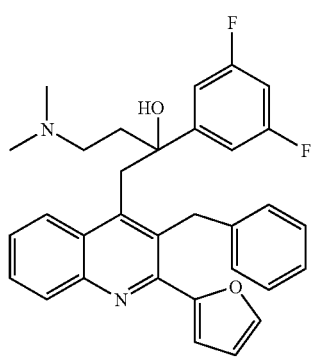

A mixture of intermediate 25, 2-furanylboronic acid (0.0012 mol), tetrakis(triphenylphosphine)palladium (0.0013 mol) and a 2M $Na_2CO_3$ solution (0.002 mol) in dimethyl ether (7 ml) was stirred at 90° C. overnight, then poured out into $H_2O$ and extracted with DCM. The organic layer was separated, dried ($MgSO_4$), filtered, and the solvent was evaporated. The residue (0.2 g) was purified by column chromatography over silica gel (eluent: DCM/MeOH 95/5; 15-40 μm). The pure fractions were collected and the solvent was evaporated. The residue (0.12 g) was purified by column chromatography over silica gel (eluent: DCM/MeOH/$NH_4OH$ 99/1/0.1; 20 μm). The pure fractions were collected and the solvent was evaporated, yielding 0.06 g of compound 5 (28%, M.P.: 130° C.).

The following final compounds were prepared according to the method described above.

compound 39

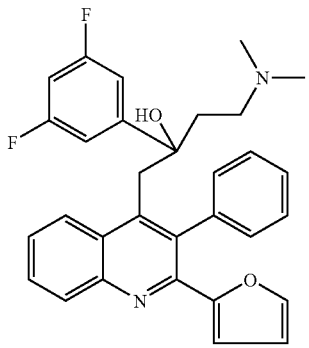

(M. P.: 136° C.)

compound 40

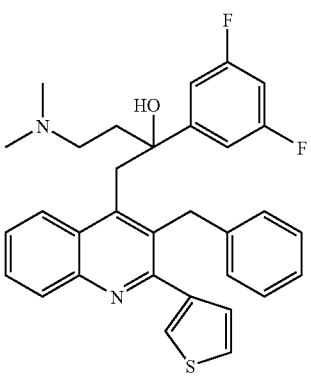

(M. P.: 173° C.)

compound 41

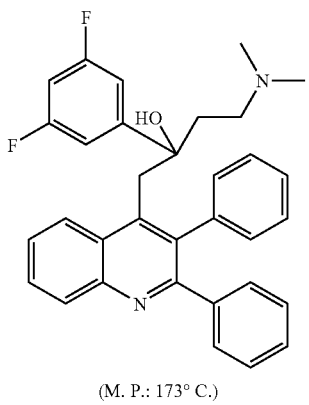

(M. P.: 173° C.)

compound 42

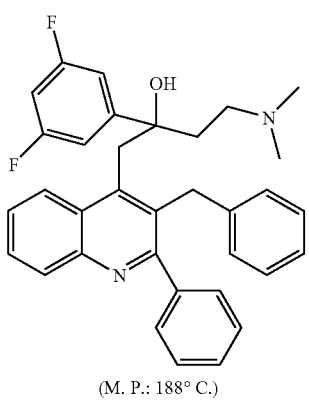

(M. P.: 188° C.)

d) Preparation of Compound 6

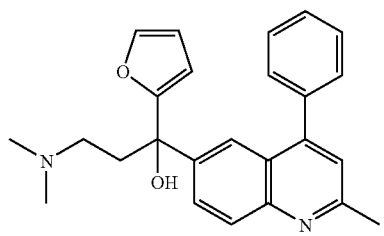

A mixture of intermediate 35 (0.0005 mol), methylboronic acid (0.0011 mol), tetrakis(triphenylphosphine)palladium (0.0005 mol) and a 2M $K_2CO_3$ solution (0.0028 mol) in dimethyl ether (10 ml) and MeOH (3 ml) was stirred at 100° C. for 24 hours, then cooled to room temperature. $H_2O$ was added. The mixture was extracted with EtOAc. The organic layer was washed with saturated NaCl, dried ($MgSO_4$), filtered and the solvent was evaporated. The residue (0.19 g) was purified by column chromatography over kromasil (eluent: DCM/MeOH/$NH_4OH$ 95/5/0.1; 10 µm). The pure fractions were collected and the solvent was evaporated, yielding 0.06 g of compound 6 (28%, MH+: 387, oil).

The following final compound was prepared according to the method described above.

compound 43

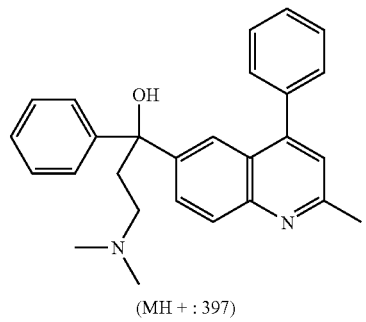

(MH+: 397)

e) Preparation of Compound 7

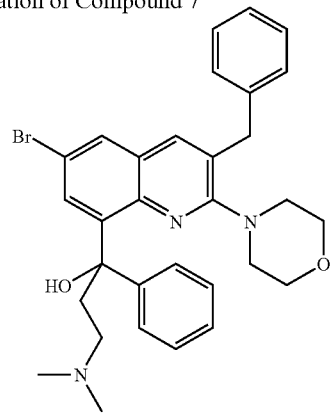

A mixture of intermediate 23 (0.0019 mol), morpholine (0.0021 mol) and $K_2CO_3$ (0.3 g) in acetonitrile (10 ml) was stirred and refluxed overnight poured out on ice and extracted with DCM. The organic layer was separated, dried ($MgSO_4$), filtered, and the solvent was evaporated. The residue (0.58 g) was purified by column chromatography over silica gel (eluent DCM/MeOH/$NH_4OH$ 95/5/01 to 9416/0.5; 15-40 µm). The desired fraction was collected and the solvent was evaporated. The obtained residue (0.04 g) was crystallized from DIPE. The precipitate was filtered off and dried, yielding 0.023 g of compound 7 (M.P.: 70° C.).

The following final compounds were prepared according to the method described above.

compound 44

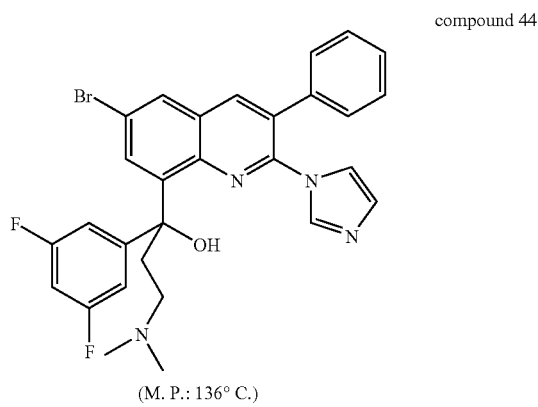

(M. P.: 136° C.)

compound 45

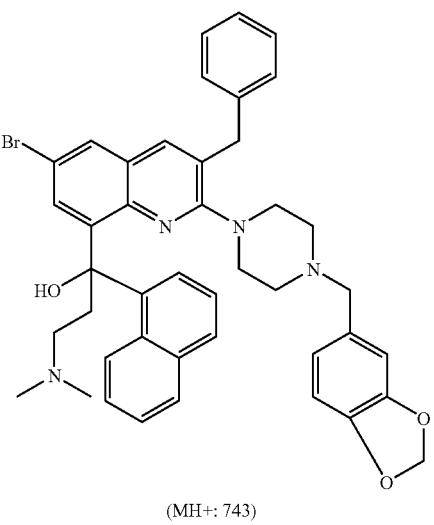

(MH+: 743)

compound 46

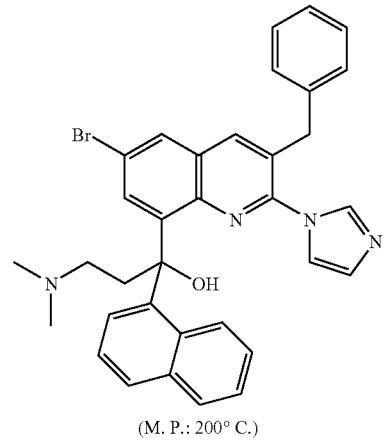

(M. P.: 200° C.)

compound 47
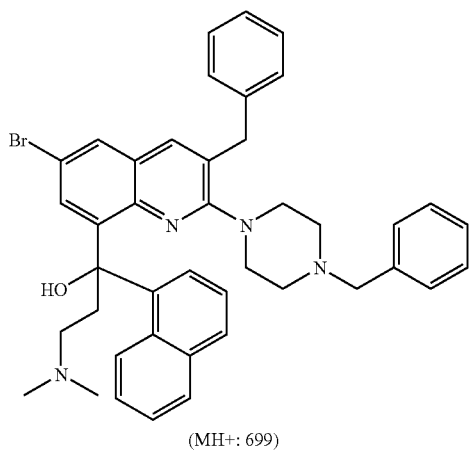
(MH+: 699)
compound 48
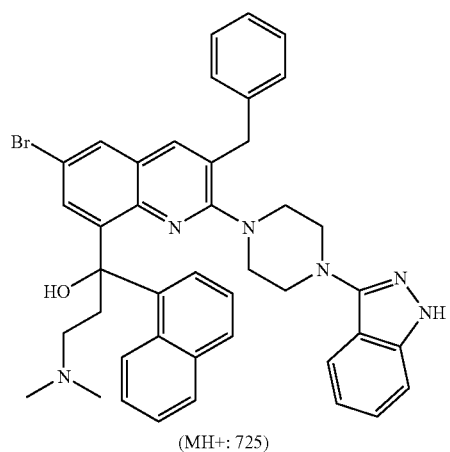
(MH+: 725)
compound 49
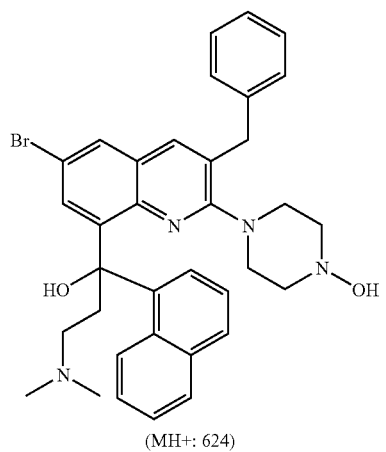
(MH+: 624)
compound 50
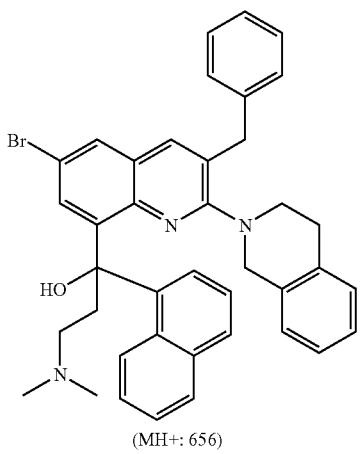
(MH+: 656)
compound 51
(MH+: 610)
compound 52
(MH+: 594)
compound 53
(M. P.: 163° C.)

compound 54
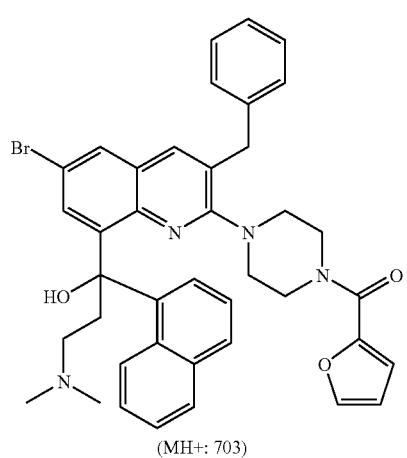
(MH+: 703)
compound 55
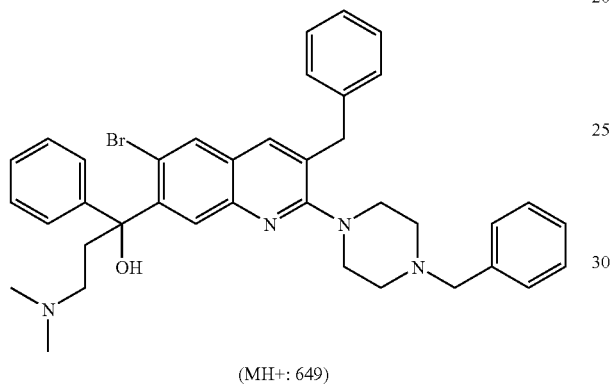
(MH+: 649)
compound 56
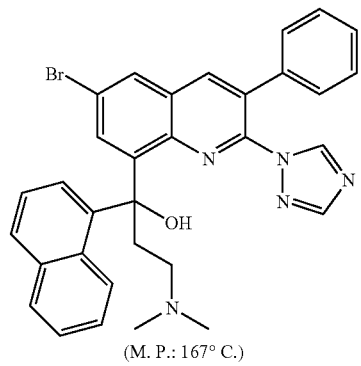
(M. P.: 167° C.)
compound 57
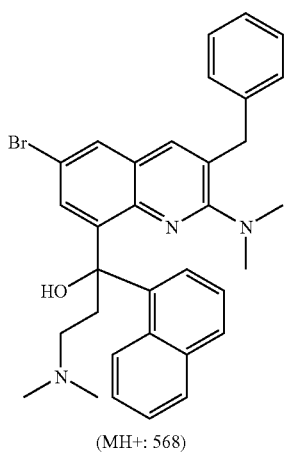
(MH+: 568)
compound 58
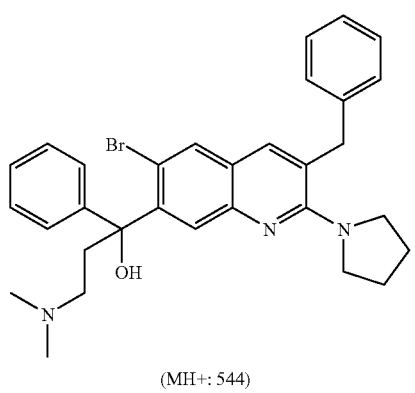
(MH+: 544)
compound 59
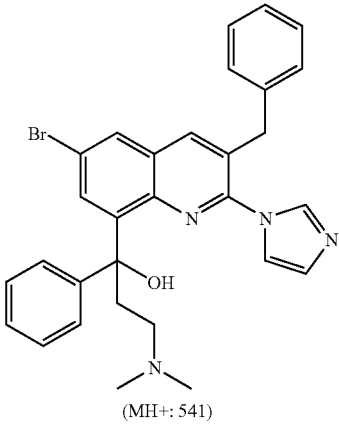
(MH+: 541)
compound 60
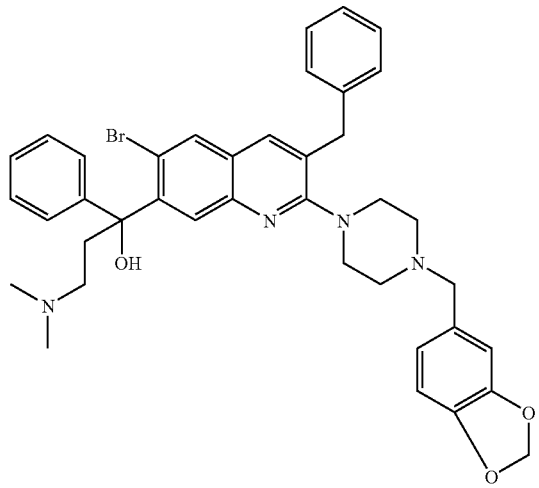
(MH+: 693)

compound 61
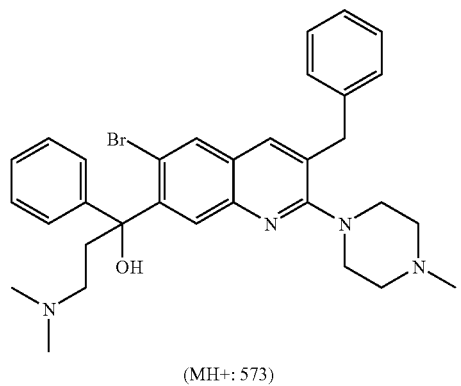
(MH+: 573)
compound 62
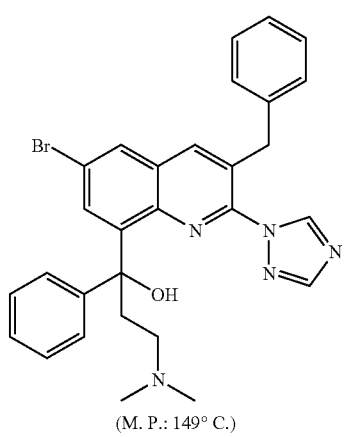
(M. P.: 149° C.)
compound 63
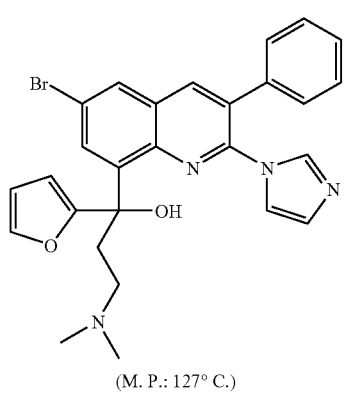
(M. P.: 127° C.)
compound 64
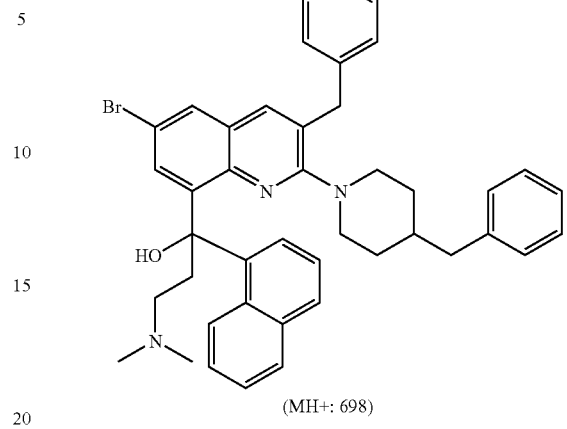
(MH+: 698)
compound 65
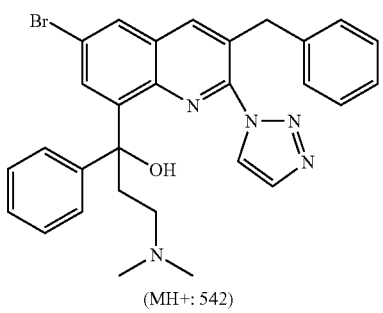
(MH+: 542)
compound 66
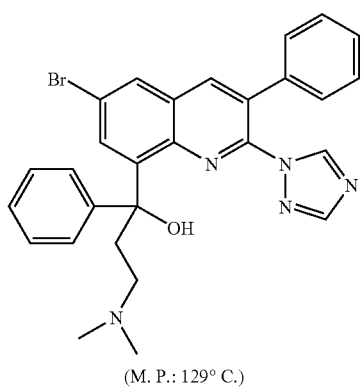
(M. P.: 129° C.)
compound 67
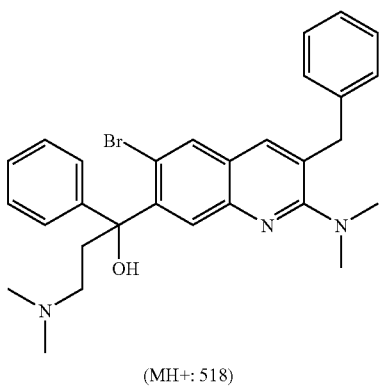
(MH+: 518)

61
-continued compound 68

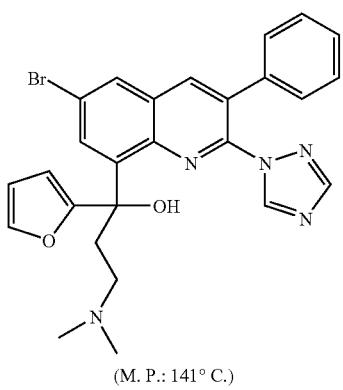

(M. P.: 141° C.)

compound 69

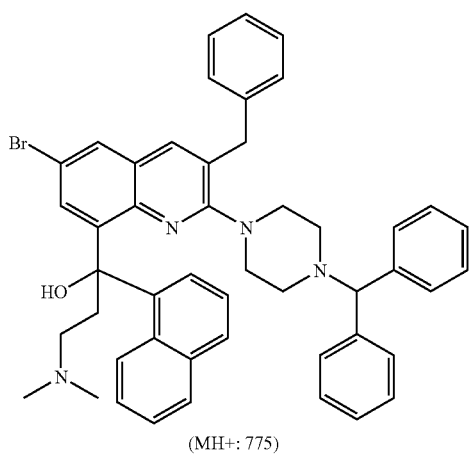

(MH+: 775)

compound 70

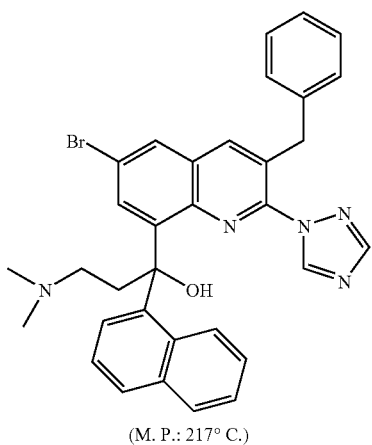

(M. P.: 217° C.)

62 f) Preparation of Compound 8

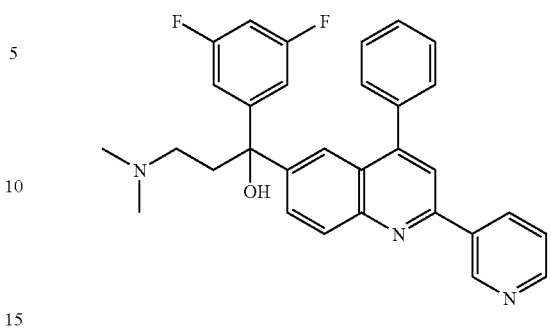

A mixture of intermediate 27 (0.0005 mol), 3-(1,3,2-dioxaborinan-2-yl)pyridine (0.0008 mol), tetrakis(triphenylphosphine)palladium (0.0005 mol) and a 2M $K_2CO_3$ solution (0.0027 mol) in dimethyl ether (7 ml) and MeOH (3 ml) was stirred at 100° C. for 18 hours under $N_2$ flow, then cooled to room temperature. $H_2O$ was added. The mixture was extracted with EtOAc. The organic layer was washed with saturated NaCl, dried ($MgSO_4$), filtered, and the solvent was evaporated. The residue (0.34 g) was taken up in 2-propanone (6 ml). Oxalic acid was added. The mixture was stirred. The precipitate was filtered off and dried at 60° C. under a vacuo, yielding 0.29 g of compound 8 as an ethanedioic acid salt (1:2) (80%, M.P.: 151° C.).

The following final compounds were prepared according to the method described above.

compound 71

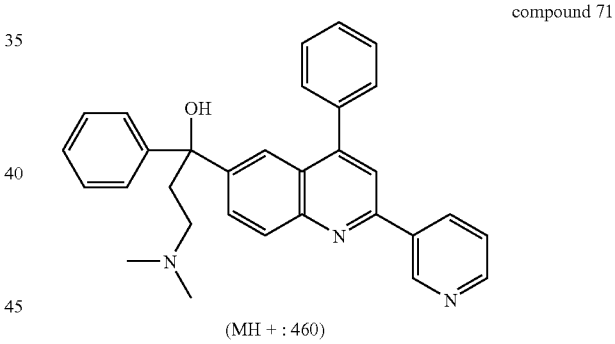

(MH + : 460)

compound 72

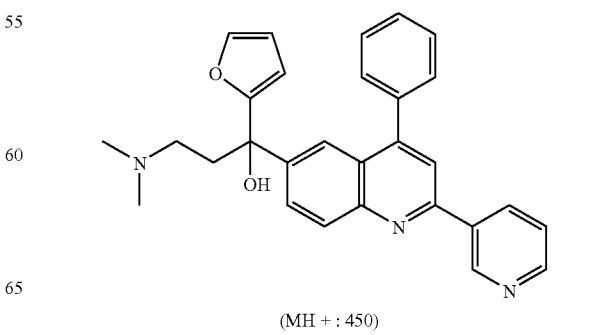

(MH + : 450)

g) Preparation of Compound 9

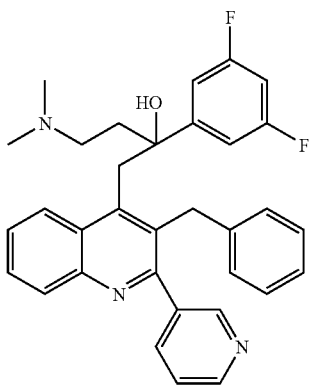

A mixture of intermediate 25 (0.0004 mol), 3-(1,3,2-dioxaborinan-2-yl)pyridine (0.0012 mol), tetrakis(triphenylphosphine)palladium (0.00004 mol) and a 2M $Na_2CO_3$ solution (0.002 mol) in dimethyl ether (6 ml) was stirred at 90° C. overnight, poured out into $H_2O$ and extracted with DCM. The organic layer was separated, dried ($MgSO_4$), filtered, and the solvent was evaporated. The residue (0.33 g) was purified by column chromatography over silica gel (eluent: DCM/MeOH/$NH_4OH$ 97/3/0.1; 20 μm). The desired fraction was collected and the solvent was evaporated, yielding 0.03 g of compound 9 (14%, M.P.: 164° C.).

h) Preparation of Compound 10

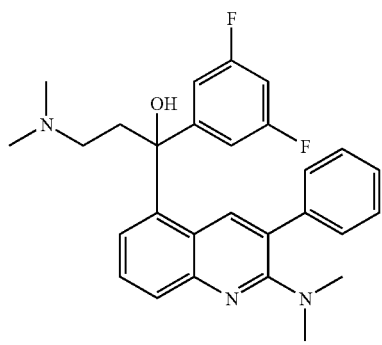

A mixture of intermediate 37 (0.0007 mol) in N-methylmethanamine (10 ml) and acetonitrile (10 ml) was stirred at 90° C. for 12 hours, poured out into $H_2O/K_2CO_3$ and extracted with DCM. The organic layer was separated, dried ($NgSO_4$), filtered, and the solvent was evaporated. The obtained fraction (0.25 g) was stirred at 90° C. for 72 hours and purified by column chromatography over kromasil (eluent: DCM/MeOH 99/1; 10 μm). The desired product fraction was collected and the solvent was evaporated. The residue (0.08 g) was dissolved in oxalic acid/2-propanol and converted into the ethanedioic acid salt (1:2.5). The precipitate was filtered off and dried, yielding 0.07 g of compound 10 (14%, M.P.: 136° C.).

The following final compounds were prepared according to the method described above.

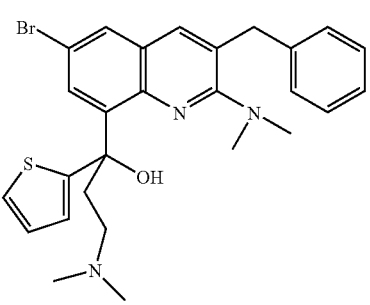

compound 73

(MH+ : 524)

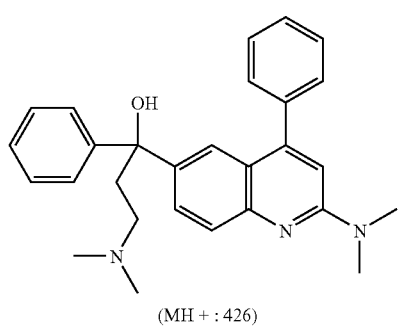

compound 74

(MH+ : 426)

i) Preparation of Compound 11

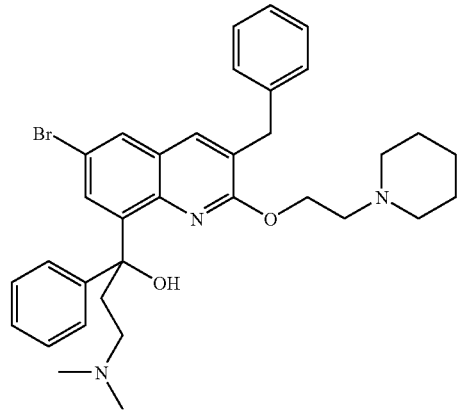

A mixture of KOH (0.0011 mol) in 1-piperidinoethanol (2 ml) was stirred at 80° C. till KOH disappeared. Intermediate 23 (00009 mol) was added. The mixture was stirred at 80° C. overnight, poured out on ice and extracted with DCM. The organic layer was separated, dried ($MgSO_4$), filtered, and the solvent was evaporated. The residue (2.49 g) was crystallized from DIPE. The precipitate was filtered off and dried, yielding 0.308 g of compound 11 (K.P.: 131° C.).

The following final compound was prepared according to the method described above.

compound 75

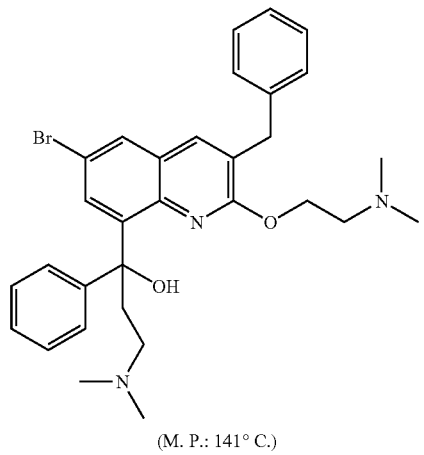

(M. P.: 141° C.)

j) Preparation of Compound 78

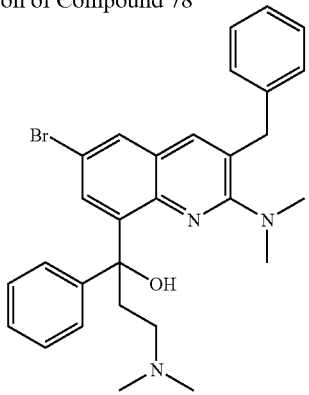

A mix of intermediate 23 (0.000137 mol), N-methylmethanamine (0.000412 mol. 3 equiv.) and K₂CO₃ (3 equiv.) in acetonitrile (2 ml) was stirred at 80° C. for 12 hours, poured out into H₂O and extracted with DCM. The organic layer was separated, dried (MgSO₄), filtered, and the solvent was evaporated. The obtained fraction was purified by column chromatography over silica gel, then the desired product fraction was collected and the solvent was evaporated, yielding 0.07 g of compound 78 (54.79%, MH+: 518).

The following final compounds were prepared according to the method described above.

compound 79

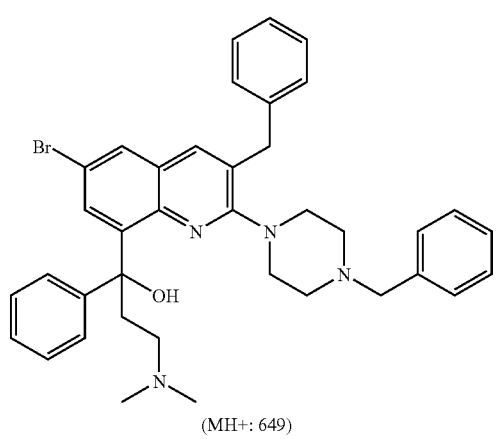

(MH+: 649)

compound 80

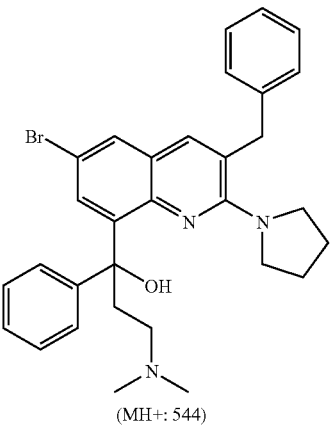

(MH+: 544)

compound 81

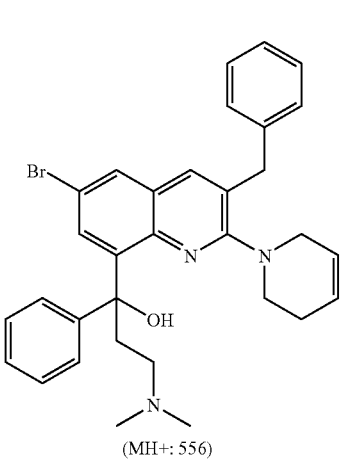

(MH+: 556)

compound 82

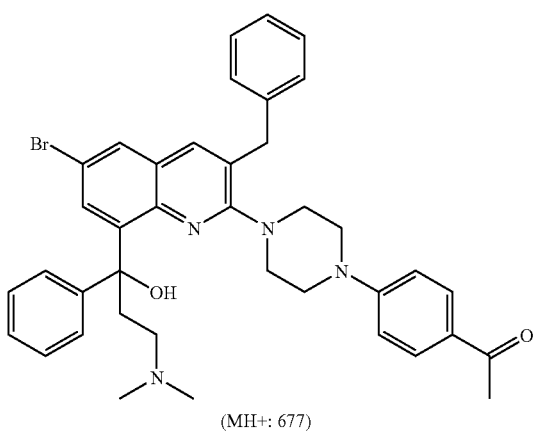

(MH+: 677)

compound 83
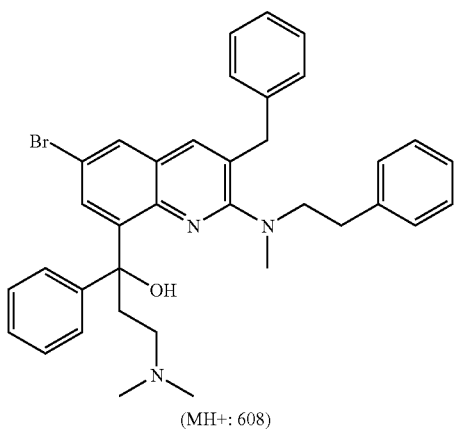
(MH+: 608)
compound 84
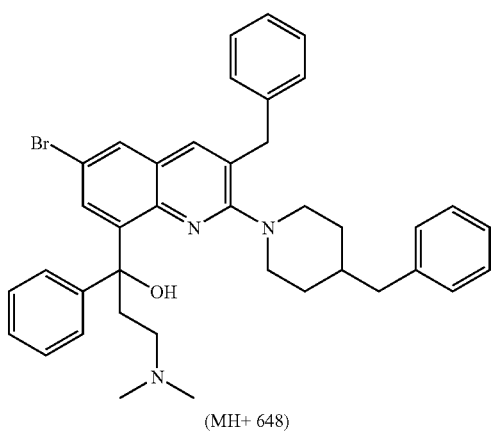
(MH+ 648)
compound 85
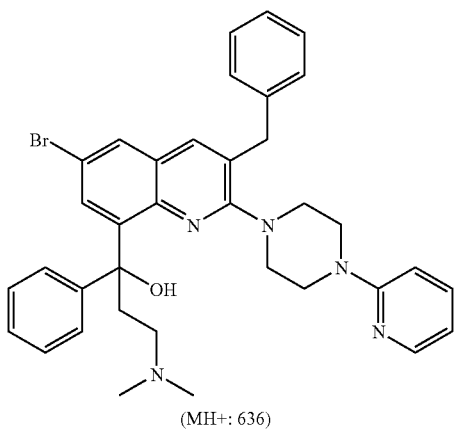
(MH+: 636)
compound 86
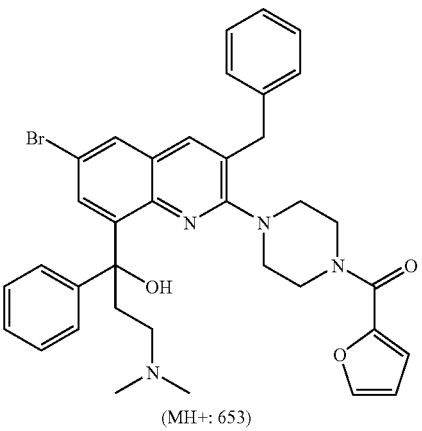
(MH+: 653)
compound 87
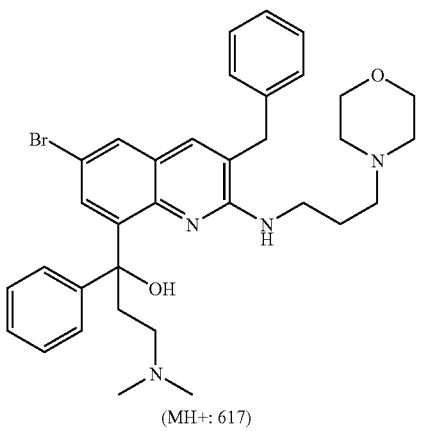
(MH+: 617)
compound 88
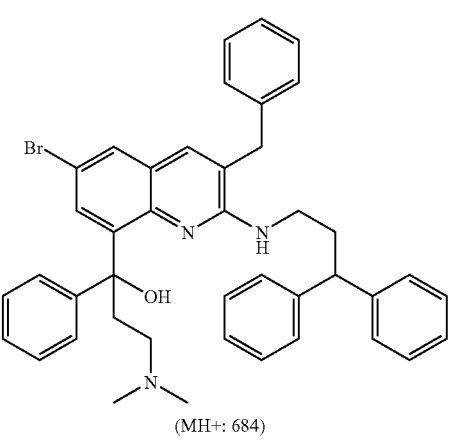
(MH+: 684)

compound 89
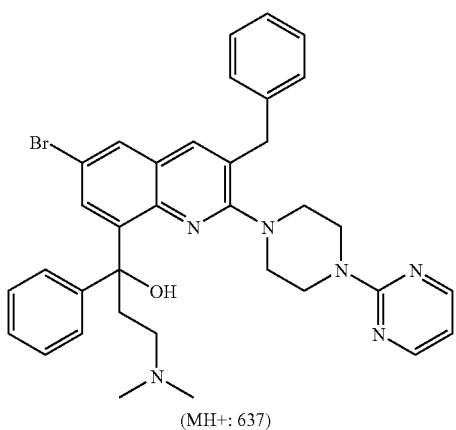
(MH+: 637)
compound 90
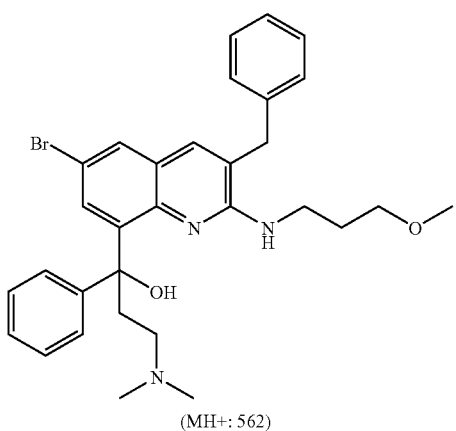
(MH+: 562)
compound 91
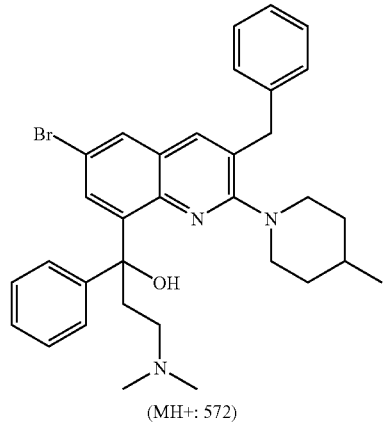
(MH+: 572)
compound 92
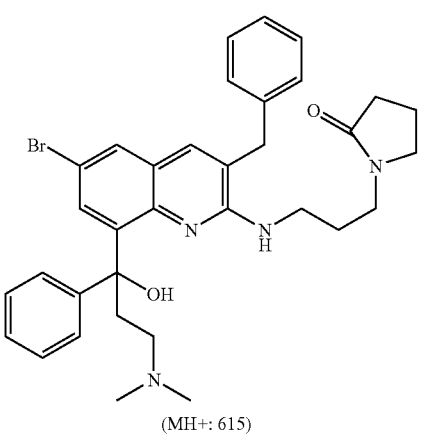
(MH+: 615)
compound 93
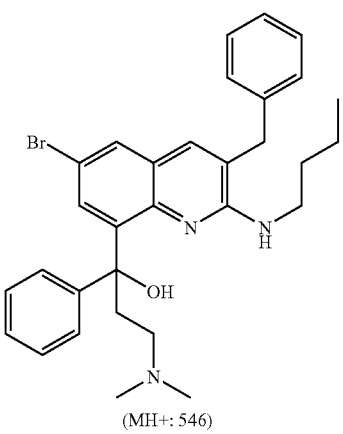
(MH+: 546)
compound 94
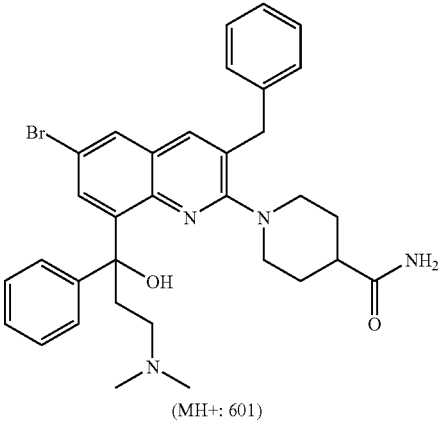
(MH+: 601)

Example B3 a) Preparation of Compound 13

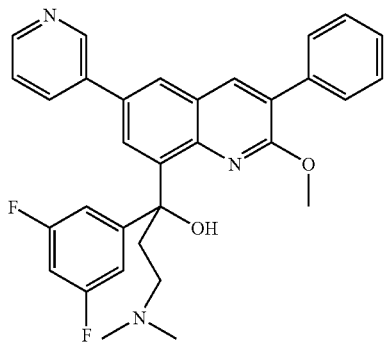

A mixture of compound 12 (0.0003 mol), 3-(1,3,2-dioxaborinan-2-yl)pyridine (0.0006 mol), tetrakis(triphenylphosphine)palladium (0.00003 mol) and a 2M $K_2CO_3$ solution (0.0015 mol) in dimethyl ether (6 ml) and MeOH (2 ml) was stirred at 100° C. for 18 hours under $N_2$ flow, then cooled to room temperature. $H_2O$ was added. The mixture was extracted with EtOAc. The organic layer was washed with saturated NaCl, dried ($MgSO_4$), filtered, and the solvent was evaporated. The residue (0.14 g) was taken up in 2-propanone (2 ml). Oxalic acid (2 equivalents) was added. The mixture was stirred for 10 minutes. The precipitate was filtered, washed with 2-propanone and dried at 70° C. under a vacuo, yielding 0.077 g of compound 13 as ethanedioic acid salt (1:1.5) (38%, M.P.: 156° C.).

The following final compound was prepared according to the method described above.

b) Preparation of Compound 14

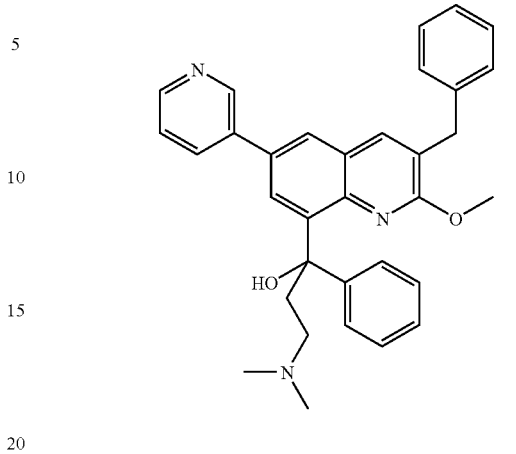

A mixture of compound 3 (0.0003 mol), tetrakis(triphenylphosphine)palladium (0.00003 mol), a 2M $Na_2CO_3$ solution (0.0019 mol) and 3-(1,3,2-dioxaborinan-2-yl)pyridine (0.0011 mol) in dimethyl ether (6 ml) was stirred at 100° C. overnight, then poured out into $H_2O$ and extracted with DCM. The organic layer was separated, dried ($MgSO_4$), filtered, and the solvent was evaporated. The residue was purified by column chromatography over kromasil (eluent: toluene/2-propanol/$NH_4OH$ 80/20/1; 10 μm). The pure fractions were collected and the solvent was evaporated. The residue (0.1 g, 51%) was crystallized from DIPE/acetonitrile. The precipitate was filtered off and dried, yielding 0.057 g of compound 14 (M.P.: 180° C.).

The following final compound was prepared according to the method described above.

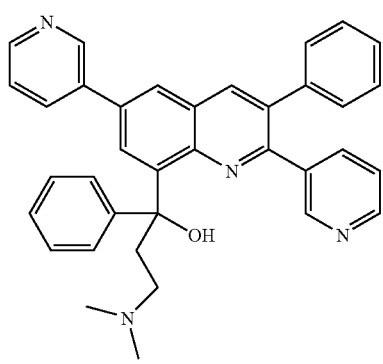

compound 76

(M. P.: 177° C.)

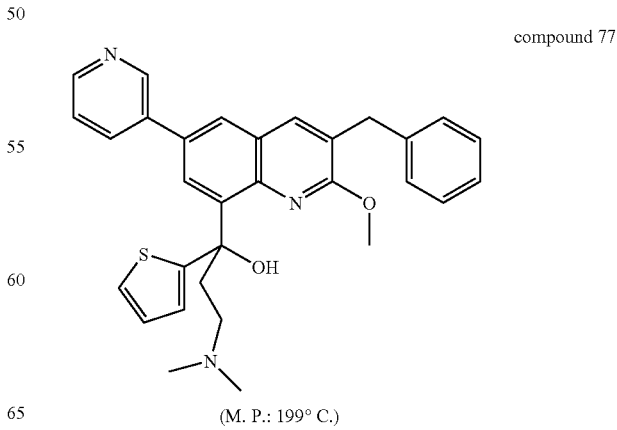

compound 77

(M. P.: 199° C.)

c) Preparation of Compound 16

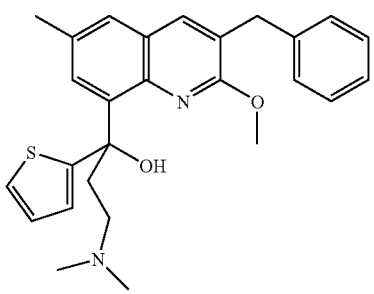

A mixture of compound 15 (0.0007 mol), tetrakis(triphenylphosphine)palladium (0.00007 mol) and tetramethylstannane (0.0016 mol) in toluene (6 ml) was stirred and refluxed overnight. H$_2$O was added. The mixture was extracted with DCM. The organic layer was separated, dried (MgSO$_4$), filtered, and the solvent was evaporated. The residue was purified by column chromatography over silica gel (eluent: DCM/MeOH/NH$_4$OH 95/5/0.3; 20 μm). The pure fictions were collected and the solvent was evaporated, yielding 0.038 g of compound 16 (11%, MH+: 447).

Example B4

Preparation of Compound 17

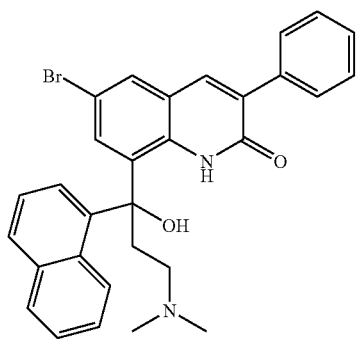

A mixture of intermediate 32 (0.0016 mol) in 6N HCl (5 ml) and THF (10 ml) was stirred at 80° C. for 48 hours, then cooled to room temperature, poured out into a 10% K$_2$CO$_3$ solution and extracted with EtOAc. The organic layer was washed with saturated NaCl, dried (MgSO$_4$), filtered and the solvent was evaporated. The residue was crystallized from diethyl ether/2-propanone. The precipitate was filtered off and dried. Part of this fraction (0.3 g of 0.6 g (44%)) was taken up in hot 2-propanone. The precipitate was filtered off and dried, yielding 0.2 g of compound 17 (15%, M.P.: 190° C.).

C. Analytical Methods

The mass of the compounds was recorded with LCMS (liquid chromatography mass spectrometry). Three methods were used which are described below. The data are gathered in Table 1 below.

LCMS-Method 1

LCMS analysis was carried out (electrospray ionization in positive mode, scanning mode from 100 to 900 amu) on a Kromasil C18 column (Interchirn, Montlucon, FR; 5 μm, 4.6×150 mm) with a flow rate of 1 ml/minute. Two mobile phases (mobile phase A. 30% 6.5 mM ammonium acetate+40% acetonitrile+30% a formic acid (2 ml/l); mobile phase B: 100% acetonitrile) were employed to run a gradient condition from 100% A for 1 minute to 100% B in 4 minutes, 100% B for 5 minutes to 100% A in 3 minutes, and reequilibrate with 100% A for 2 minutes.

LCMS-Method 2

LCMS analysis was carried out (eleetrospray ionization in both positive and negative (pulsed) mode scanning from 100 to 1000 amu) on a Kromasil C18 column (Interchim, Montlucon, FR; 3.5 μm, 4.6×100 mm) with a flow rate of 0.8 ml/minute. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A for 1 minute to 100% B in 4 minutes, 100% B at a flow rate of 1.2 ml/minute for 4 minutes to 100% A at 0.8 ml/minute in 3 minutes, and reequilibrate with 100% A for 1.5 minute.

LCMS-Method 3

LCMS analysis was carried out (electrospray ionization in positive mode, scanning from 100 to 900 amu) on a Xterra MS C18 column (Waters, Milford, Mass.; 5 μm, 4.6×150 mm) with a flow rate of 1 ml/minute. Two mobile phases (mobile phase A: 85% 6.5 mM ammonium acetate+15% acetonitrile; mobile phase B: 20% 6.5 mM ammonium acetate+80% acetonitrile) were employed to run a gradient condition from 100% A for 3 minutes to 100% B in 5 minutes, 100%o B at a flow rate of 1.2 ml/minute for 6 minutes to 100% A at 0.8 ml/minute in 3 minutes, and reequillbrate with 100% A for 3 minutes.

TABLE 1

| | LCMS parent peak |
| --- | --- |
| Compound No | LC/GC/MS Method |
| 1 | 1 |
| 4 | 3 |
| 6 | 2 |
| 16 | 2 |
| 18 | 1 |
| 19 | 1 |
| 21 | 1 |
| 22 | 1 |
| 23 | 1 |
| 28 | 1 |
| 29 | 1 |
| 31 | 1 |
| 35 | 1 |
| 43 | 3 |
| 45 | 2 |
| 47 | 2 |
| 48 | 2 |
| 49 | 2 |
| 50 | 2 |
| 51 | 2 |
| 52 | 2 |
| 54 | 2 |
| 55 | 1 |
| 57 | 2 |
| 58 | 1 |
| 59 | 1 |
| 60 | 1 |
| 61 | 1 |
| 64 | 2 |
| 65 | 1 |
| 67 | 1 |
| 69 | 2 |
| 71 | 3 |
| 72 | 3 |
| 73 | 1 |
| 74 | 3 |
| 78 | 1 |
| 79 | 1 |
| 80 | 1 |

TABLE 1-continued

LCMS parent peak

| Compound No | LC/GC/MS Method |
|---|---|
| 81 | 1 |
| 82 | 1 |
| 83 | 1 |
| 84 | 1 |
| 85 | 1 |
| 86 | 1 |
| 87 | 1 |
| 88 | 1 |
| 89 | 1 |
| 90 | 1 |
| 91 | 1 |
| 92 | 1 |
| 93 | 1 |
| 94 | 1 |

D. Pharmacological Examples

D.1. In-vitro Method for Testing Compounds Against *M. tuberculosis*.

Flat-bottom, sterile 96-well plastic microtiter plates were filled with 100 μl of Middlebrook (1×) broth medium. Subsequently, stock solutions (10× final test concentration) of compounds were added in 25 μl volumes to a series of duplicate wells in column 2 so as to allow evaluation of their effects on bacterial growth. Serial five-fold dilutions were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 5000 CFU per well of *Mycobacterium tuberculosis* (strain H37RV), m a volume of 100 μl in Middlebrook (1×) broth medium, was added to the rows A to H, except column 12. The same volume of broth medium without inoculum was added to column 12 in row A to H. The cultures were incubated at 37° C. for 7 days in a humidified atmosphere (incubator with open air valve and continuous ventilation). One day before the end of incubation, 6 days after inoculation, Resazurin (1:5) was added to all wells in a volume of 20 μl and plates were incubated for another 24 hours at 37° C. On day 7 the bacterial growth was quantitated fluorometrically.

The fluorescence was read in a computer-controlled fluorometer (Spectramax Gemini EM, Molecular Devices) at an excitation wavelength of 530 nm and an emission wavelength of 590 nm. The percentage growth inhibition achieved by the compounds was calculated according to standard methods, and MIC data (representing IC90's expressed in microgram/ml) were calculated.

D.2. In-vitro Method for Testing Compounds for Anti-bacterial Activity Against Strain *M. Smegmatis* ATCC607.

Flat-bottom, sterile 96well plastic microtiter plates were filled with 180 μl of sterile deionized water, supplemented with 0.25% BSA. Subsequently, stock solutions (7.8× final test concentration) of compounds were added in 45 μl volumes to a series of duplicate wells in column 2 so as to allow evaluation of their effects on bacterial growth. Serial five-fold dilutions (45 μl in 180 μl) were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 250 CFU per well of bacteria inoculum, in a volume of 100 μl in 2.8× Mueller-Hinton broth medium, was added to the rows A to H, except column 12. The same volume of broth medium without inoculum was added to column 12 in row A to H. The cultures were incubated at 37° C. for 48 hours in a humidified 5% $CO_2$ atmosphere (incubator with open air valve and continuous ventilation). At the end of incubation, two days after inoculation, the bacterial growth was quantitated fluorometrically. Therefore Alamar Blue (10×) was added to all wells in a volume of 20 μl and plates were incubated for another 2 hours at 50° C.

The fluorescence was read in a computer-controlled fluorometer (Cytofluor, Biosearch) at an excitation wavelength of 530 nm and an emission wavelength of 590 nm (gain 30). The % growth inhibition achieved by the compounds was calculated according to standard methods. The $pIC_{50}$ was defined as the 50% inhibitory concentration for bacterial growth. The results are shown in Table 2

TABLE 2

Results ($pIC_{50}$) of an in vitro-screening of the compounds according to the invention for *M. smegmatis* and *M. tuberculosis*.

| Co. No. | *M. smegmatis* ($pIC_{50}$) | *M. tuberculosis* ($pIC_{50}$) |
|---|---|---|
| 1 | 5.9 | |
| 2 | 5.9 | |
| 3 | 5.9 | |
| 4 | 6.6 | |
| 5 | 6.4 | |
| 6 | 4.5 | |
| 7 | 5.8 | |
| 8 | 5.8 | |
| 9 | 5.2 | |
| 10 | 5.7 | |
| 11 | 5.5 | 5.5 |
| 12 | 5.8 | |
| 13 | 6.4 | |
| 14 | 5.1 | |
| 15 | 5.1 | |
| 16 | 5.8 | |
| 18 | 5.8 | |
| 19 | 5.1 | |
| 20 | 4.5 | |
| 21 | 4.5 | |
| 26 | 5.7 | |
| 27 | 5.2 | |
| 28 | 5.1 | |
| 29 | 4.5 | |
| 31 | 5.9 | |
| 32 | 5.0 | |
| 33 | 4.5 | |
| 35 | 5.8 | |
| 36 | 5.0 | |
| 37 | 4.1 | |
| 39 | 5.9 | |
| 40 | 5.1 | |
| 41 | 4.5 | |
| 42 | 4.4 | |
| 43 | 4.9 | |
| 44 | 5.9 | |
| 45 | 6.6 | |
| 46 | 6.6 | |
| 47 | 6.4 | |
| 48 | 6.2 | |
| 49 | 6.1 | |
| 50 | 6.1 | |
| 51 | 6.0 | |
| 52 | 6.0 | |
| 53 | 5.9 | |
| 54 | 5.9 | |
| 55 | 5.9 | |
| 56 | 5.8 | |
| 57 | 5.8 | |
| 58 | 5.8 | |

TABLE 2-continued

Results (pIC$_{50}$) of an in vitro-screening of the compounds according to the invention for M. smegmatis and M. tuberculosis.

| Co. No. | M. smegmatis (pIC$_{50}$) | M. tuberculosis (pIC$_{50}$) |
|---|---|---|
| 59 | 5.8 | |
| 60 | 5.7 | |
| 61 | 5.3 | |
| 62 | 5.3 | |
| 63 | 5.2 | |
| 64 | 5.2 | |
| 65 | 5.2 | |
| 66 | 4.9 | |
| 67 | 4.7 | |
| 68 | 4.5 | |
| 69 | 4.4 | |
| 71 | 5.8 | |
| 72 | 5.2 | |
| 73 | 5.8 | |
| 75 | 5.2 | 5.3 |
| 76 | 5.8 | |
| 77 | 4.9 | |
| 78 | 5.8 | |
| 79 | 6.2 | 4.6 |
| 80 | 6.1 | 5.05 |
| 81 | 5.9 | |
| 82 | 5.8 | |
| 83 | 5.8 | |
| 84 | 5.7 | |
| 85 | 5.7 | |
| 86 | 5.7 | |
| 87 | 5.6 | |
| 88 | 5.6 | |
| 89 | 5.6 | |
| 90 | 5.5 | |
| 91 | 5.3 | |
| 92 | 5.2 | |
| 93 | 5.1 | |
| 94 | 5.1 | |

The invention claimed is:

1. A compound according to the Formula (Ia) or the Formula (Ib)

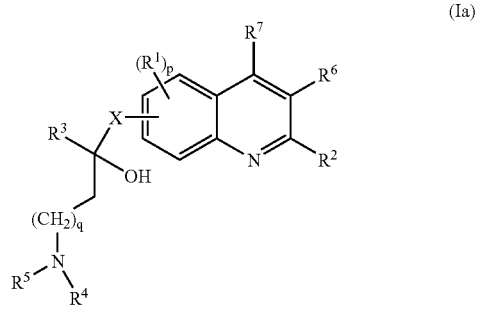

(Ia)

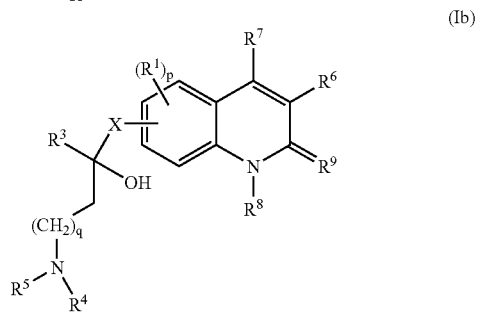

(Ib)

the pharmaceutically acceptable acid or base addition salts thereof, the quaternary amines thereof, the stereochemically isomeric forms thereof, the tautomeric forms thereof and the N-oxide forms thereof, wherein :

$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2 or 3;

$R^2$ is hydrogen; alkyl; hydroxy; thio; alkyloxy optionally substituted with amino or mono or di(alkyl)amino or a radical of formula

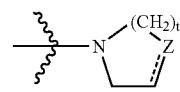

wherein Z is $CH_2$, $CH-R^{10}$, O, S, $N-R^{10}$ and t is an integer equal to 1 or 2 and the dotted line represents an optional bond; alkyloxyalkyloxy; alkylthio; mono or di(alkyl)amino wherein alkyl may optionally be substituted with one or two substituents each independently be selected from alkyloxy or Ar or Het or morpholinyl or 2-oxopyrrolidinyl; Ar; Het or a radical of formula

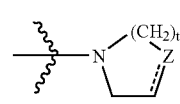

wherein Z is $CH_2$, $CH-R^{10}$, O, S, $N-R^{10}$; t is an integer equal to 1 or 2; and the dotted line represents an optional bond;

$R^3$ is alkyl, Ar, Ar-alkyl, Het or Het-alkyl;

q is an integer equal to zero, 1, 2, 3 or 4;

X is a direct bond or $CH_2$;

$R^4$ and $R^5$ each independently are hydrogen, alkyl or benzyl; or $R^4$ and $R^5$ together and including the N to which they are attached may form a radical selected from the group of pyrrolidinyl, 2H-pyrrolyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, each of said rings optionally being substituted with alkyl, halo, haloalkyl, hydroxy, alkyloxy, amino, mono- or dialkylamino, alkylthio, alkyloxyalkyl, alkylthioalkyl and pyrimidinyl;

$R^6$ is hydrogen or a radical of formula

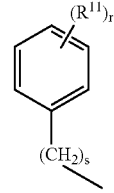

wherein s is an integer equal to zero, 1, 2, 3 or 4; r is an integer equal to 1, 2, 3, 4 or 5; and $R^{11}$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^{11}$ radicals may be taken together to form together with the phenyl ring to which they are attached a naphthyl;

$R^7$ is hydrogen, alkyl, Ar, or Het;

$R^8$ is hydrogen or alkyl;

$R^9$ is oxo; or $R^8$ and $R^9$ together form the radical —CH═CH—N═;

$R^{10}$ is hydrogen, alkyl, hydroxyl, aminocarbonyl, mono-or di(alkyl)aminocarbonyl, Ar, Het, alkyl substituted with one or two Het, alkyl substituted with one or two Ar, Het-C(═O)—, Ar—C(═O)—;

alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;

Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, alkylcarbonyl, aminocarbonyl, morpholinyl and mono- or dialkylaminocarbonyl;

Het is a monocyclic heterocycle selected from the group of N-phenoxypiperidinyl, pyrrolyl, pyrazolyl, imidazolyl, furanyl, thienyl, oxazolyl, isoxazolyl, thiazolyl, triazolyl, isothiazolyl, pyridinyl, pyrimidinyl, pyrazinyl and pyridazinyl; or a bicyclic heterocycle selected from the group of quinolinyl, isoquinolinyl, 1,2,3,4-tetrahydroisoquinolinyl, quinoxalinyl, indolyl, indazolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms.

2. A compound according to claim 1 provided that when $R^6$ is other than hydrogen then $R^7$ is hydrogen and when $R^7$ is other than hydrogen then $R^6$ is hydrogen.

3. A compound according to claim 1 wherein $R^2$ is hydrogen; alkyl; alkyloxy optionally substituted with amino or mono or di(alkyl)amino or a radical of formula

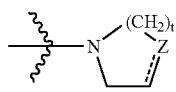

wherein Z is $CH_2$, CH—$R^{10}$, O, S, N—$R^{10}$ and t is an integer equal to 1 or 2 and the dotted line represents an optional bond; mono or di(alkyl)amino;

Ar; Het or a radical of formula

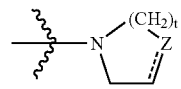

wherein Z is $CH_2$, CH—$R^{10}$, O, S, N—$R^{10}$;

t is an integer equal 1 or 2; and the dotted line represents an optional bond.

4. A compound according to claim 1 wherein $R^3$ is naphthyl, phenyl or Het, each optionally substituted with 1 or 2 substituents, that substituent being a halo or haloalkyl.

5. A compound according to claim 1 wherein q is equal to 1.

6. A compound according to claim 1 wherein $R^4$ and $R^5$ each independently are hydrogen or alkyl.

7. A compound according to claim 1 wherein $R^6$ is hydrogen or a radical of formula

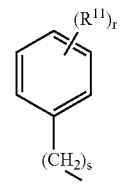

wherein s is an integer equal to zero or 1; r is an integer equal to 1 or 2.

8. A compound according to claim 1 wherein $R^7$ is hydrogen or Ar.

9. A compound according to claim 1 wherein $R^1$ is hydrogen, halo, alkyl or Het; $R^2$ is alkyl, alkyloxy optionally substituted with mono or di(alkyl)amino or a radical of formula

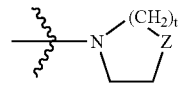

wherein Z is $CH_2$, CH—$R^{10}$, O, N—$R^{10}$, t is an integer equal to 1 or 2, and $R^{10}$ is hydrogen, alkyl, hydroxyl, alkyl substituted with one or two Het, alkyl substituted with one or two Ar, Het-C(═O)—; Ar; Het; a radical of formula

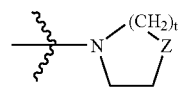

wherein Z is $CH_2$, CH—$R^{10}$, O, N—$R^{10}$; t is an integer equal to 1 or 2, wherein $R^{10}$ is hydrogen, alkyl, hydroxyl, alkyl substituted with one or two Het, alkyl substituted with one or two Ar, Het-C(═O)—; $R^3$ is Ar or Het, each optionally substituted with 1 or 2 substituents that substituent being a halo; $R^4$ and $R^5$ are each alkyl; $R^6$ is hydrogen, phenyl, benzyl or 4-methylbenzyl; $R^7$ is hydrogen or phenyl; $R^8$ is hydrogen; $R^9$ is oxo.

10. A compound according to claim 1 wherein $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2 or 3;

$R^2$ is hydrogen; alkyl; hydroxy; thio; alkyloxy optionally substituted with amino or mono or di(alkyl)amino or a radical of formula

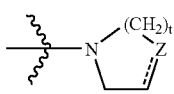

wherein Z is $CH_2$, $CH-R^{10}$, O, S, $N-R^{10}$ and t is an integer equal to 1 or 2 and the dotted line represents an optional bond; alkyloxyalkyloxy; alkylthio; mono or di(alkyl)amino wherein alkyl may optionally be substituted with one or two substituents each independently be selected from alkyloxy or Ar or Het or morpholinyl or 2-oxopyrrolidinyl; Het or a radical of formula

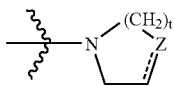

wherein Z is $CH_2$, $CH-R^{10}$, O, S, $N-R^{10}$; t is an integer equal to 1 or 2; and the dotted line represents an optional bond;

$R^3$ is alkyl, Ar, Ar-alkyl, Het or Het-alkyl;

q is an integer equal to zero, 1, 2, 3 or 4;

X is a direct bond;

$R^4$ and $R^5$ each independently are hydrogen, alkyl or benzyl; or $R^4$ and $R^5$ together and including the N to which they are attached may form a radical selected from the group of pyrrolidinyl, 2H-pyrrolyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, each of said rings optionally being substituted with alkyl, halo, haloalkyl, hydroxy, alkyloxy, amino, mono- or dialkylamino, alkylthio, alkyloxyalkyl, alkylthioalkyl and pyrimidinyl;

$R^6$ is a radical of formula

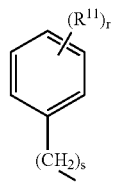

wherein s is an integer equal to zero, 1, 2, 3 or 4; r is an integer equal to 1, 2, 3, 4 or 5; and $R^{11}$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^{11}$ radicals may be taken together to form together with the phenyl ring to which they are attached a naphthyl;

$R^7$ is hydrogen, alkyl, Ar or Het;

$R^8$ is hydrogen or alkyl;

$R^9$ is oxo; or $R^8$ and $R^9$ together form the radical $-CH=CH-N=$;

$R^{10}$ is hydrogen, alkyl, aminocarbonyl, mono-or di(alkyl) aminocarbonyl, Ar, Het, alkyl substituted with one or two Het, alkyl substituted with one or two Ar, Het-C (=O)—;

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;

Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, alkylcarbonyl, aminocarbonyl, morpholinyl and mono- or dialkylaminocarbonyl;

Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrazinyl and pyridazinyl; or a bicyclic heterocycle selected from the group of quinolinyl, quinoxalinyl, indolyl, indazolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms.

11. A compound according to claim 1 wherein the compound is a compound of formula (Ia).

12. A composition comprising a pharmaceutically acceptable carrier and, as active ingredient, a therapeutically effective amount of a compound as defined in claim 1.

13. Method of treating a patient suffering from, or at risk of, a mycobacterial disease, which comprises administering to the patient a therapeutically effective amount of a compound according to claim 1 or pharmaceutical composition according to claim 12.

14. A process for preparing a compound according to claim 1 characterized by a) reacting an intermediate of formula (II) with H—R$^{2a}$ or with a suitable salt form of H—R$^{2a}$, optionally in the presence of a suitable solvent and optionally in the presence of a suitable base

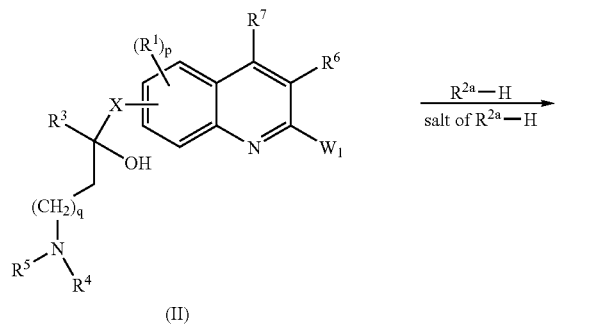

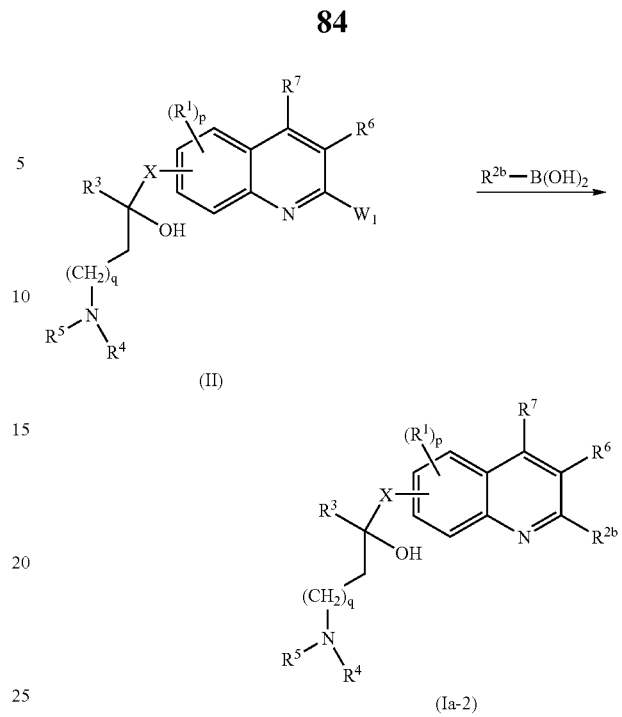

wherein W$_1$ represents a suitable leaving group, wherein R$^{2a}$ represents alkoxy; a radical of formula

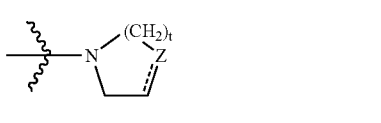

wherein t and Z are defined as in claim 1; alkyloxy substituted with a radical of formula

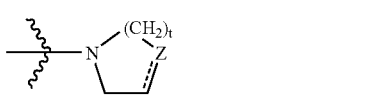

wherein t and Z are defined as in claim 1; mono or di(alkyl)amino wherein alkyl may optionally be substituted with one or two substituents each independently be selected from alkyloxy or Ar or Het or morpholinyl or 2-oxopyrrolidinyl; and wherein R$^1$, R$^3$ to R$^7$, p, q and X are defined as in claim 1;

b) reacting an intermediate of formula (II) with R$^{2b}$—B(OH)$_2$ in the presence of a suitable catalyst, a suitable solvent, and a suitable base wherein W$_1$ represents a suitable leaving group, wherein R$^{2b}$ represents Het or alkyl and wherein R$^1$, R$^3$ to R$^7$, p, q and X are defined as in claim 1;

c) reacting an intermediate of formula (II) with

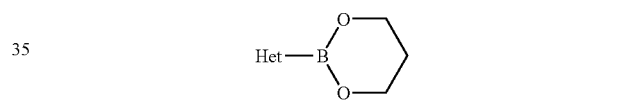

in the presence of a suitable catalyst, a suitable solvent and a suitable base,

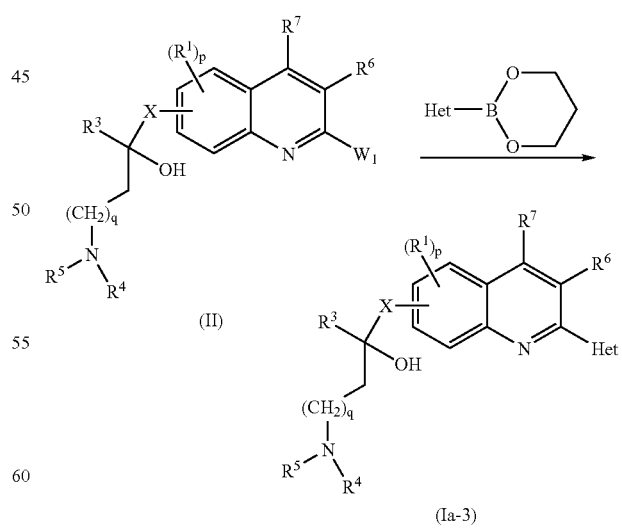

wherein W$_1$ represents a suitable leaving group and wherein R$^1$, R$^3$ to R$^7$, p, q and X are defined as in claim 1;

d) reacting an intermediate of formula (III) with an intermediate of formula (IV) in the presence of a suitable coupling agent, in the presence of a suitable solvent and optionally in the presence of a suitable base,

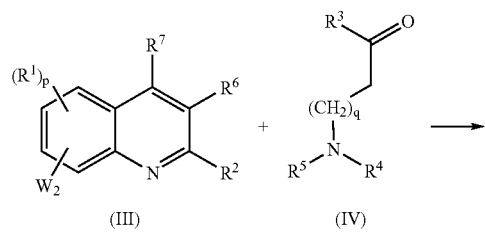

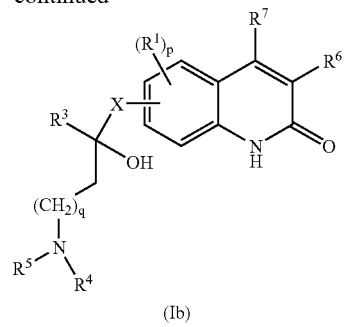

wherein $W_1$ represents a suitable leaving group and wherein $R^1$, $R^3$ to $R^7$, p, q and X are defined as in claim 1;

f) converting a compound of formula (Ia-5) into a compound of formula (Ia-6), by reaction with

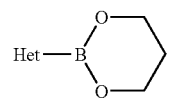

in the presence of a suitable catalyst, a suitable solvent, and a suitable base,

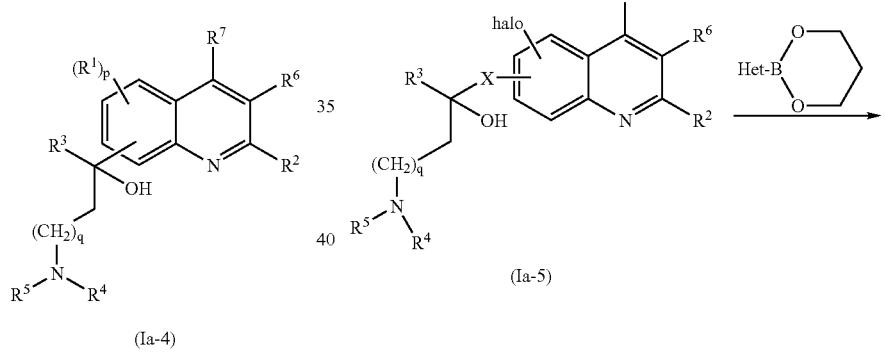

wherein $W_2$ represents a suitable leaving group and wherein $R^1$ to $R^7$, p and q are defined as in claim 1;

e) reacting an intermediate of formula (II) with a suitable acid in the presence of a suitable solvent,

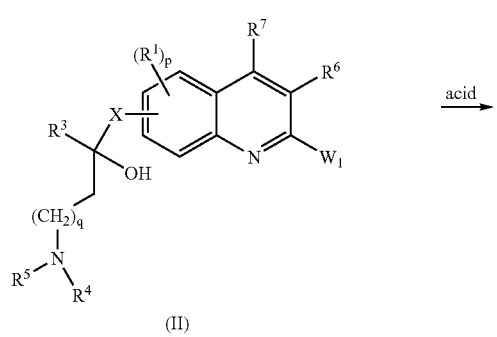

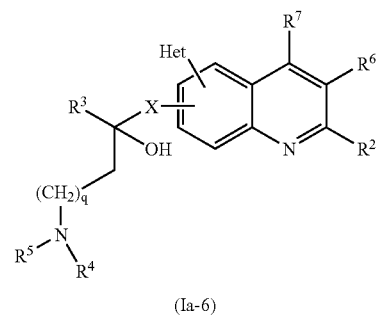

wherein $R^2$ to $R^7$, p, q and X are defined as in claim 1;

g) converting a compound of formula (Ia-5) into a compound of formula (Ia-7), by reaction with $Sn(CH_3)_4$ in the presence of a suitable catalyst and a suitable solvent,

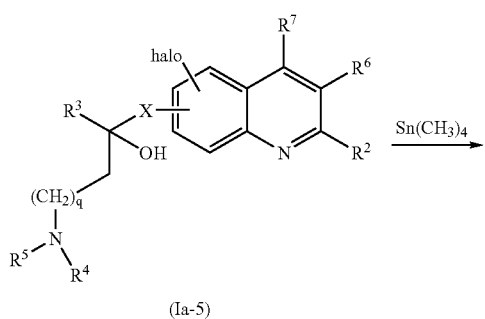

(Ia-5)

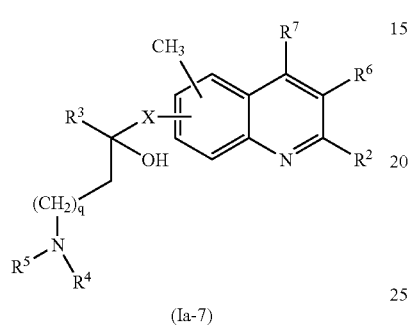

(Ia-7)

wherein $R^2$ to $R^7$, p, q and X are defined as in claim 1;

or, if desired, converting compounds of formula (Ia) or (Ib) into each other following art-known transformations, and further, if desired, converting the compounds of formula (Ia) or (Ib), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms, quaternary amines, tautomeric forms or N-oxide forms thereof.

\* \* \* \* \*